US008580956B2

(12) United States Patent
Zhu et al.

(10) Patent No.: US 8,580,956 B2
(45) Date of Patent: Nov. 12, 2013

(54) GAMMA SECRETASE MODULATORS

(75) Inventors: Zhaoning Zhu, Plainsboro, NJ (US); William J. Greenlee, Teaneck, NJ (US); Zhong-Yue Sun, Parlin, NJ (US); Gioconda Gallo, Summit, NJ (US); Ruo Xu, Watchung, NJ (US); Xianhai Huang, Warren, NJ (US); Xiaohong Zhu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 554 days.

(21) Appl. No.: 12/600,910

(22) PCT Filed: May 28, 2008

(86) PCT No.: PCT/US2008/006733
§ 371 (c)(1),
(2), (4) Date: Jun. 16, 2010

(87) PCT Pub. No.: WO2008/153792
PCT Pub. Date: Dec. 18, 2008

(65) Prior Publication Data
US 2010/0255005 A1     Oct. 7, 2010

Related U.S. Application Data

(60) Provisional application No. 60/941,396, filed on Jun. 1, 2007.

(51) Int. Cl.
*C07D 498/04*    (2006.01)
*C07D 498/14*    (2006.01)
*A61K 31/4245*   (2006.01)
*A61K 31/5365*   (2006.01)
*A61K 31/5383*   (2006.01)

(52) U.S. Cl.
USPC ............. 544/63; 544/105; 544/235; 544/250; 546/64; 546/65; 546/115; 546/116; 548/126; 548/242; 514/230.5; 514/248; 514/249; 514/293; 514/302; 514/364

(58) Field of Classification Search
USPC ............. 544/105, 235, 350; 546/64, 65, 115, 546/116; 548/126, 242; 514/230.5, 248, 514/249, 293, 302, 364
See application file for complete search history.

(56) References Cited

U.S. PATENT DOCUMENTS

| 2005/0042284 A1 | 2/2005 | Hobden et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |

FOREIGN PATENT DOCUMENTS

| WO | 9217475       | 10/1992 |
| WO | 2004071431 A2 | 8/2004  |
| WO | 2004110350 A2 | 12/2004 |
| WO | 2005110422 A2 | 11/2005 |
| WO | 2006001877 A2 | 5/2006  |
| WO | 2006045554 A1 | 5/2006  |

OTHER PUBLICATIONS

West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Bianchi, G. "2-Isoxazoline derivatives. IV. Bromination of dihydroacenaphtho[1,2-d]isoxazole derivatives." Journal of the Chemical Society [Section] C: Organic 1971 (13), 2375-81.*
Isager, Per; "Reactions with .alpha.,.beta.-unsaturated nitrile oxides. Synthetic studies in the terpene field. Synthesis of tagetones, ocimenones, deodarone, and atlantone." Acta Chemica Scandinavica, 1990, 44(8), 806-13.*
Hook V. Y.H. "Neuroproteases in Peptide Neurotransmission and Neurodegenerative Diseases Applications to Drug Discovery Research" Biodrugs 2006, 20, 105-119.*
Jhee et. al. "beta-amyloid therapies in Alzheimer's disease" Expert Opinion on Investigational Drugs 2001, 10, 593-605.*
Grazia D'Onofrio "Advances in the identification of g-secretase inhibitors for thetreatment of Alzheimer's disease" Expert Opinion on Investigational Drugs 2012, 7, 20-37.*
Bode, et al., "A Mild and Chemoselective Method for the Reductionof Conjugated Isoxazolines to β-Hydroxy Ketones," Organic Letters, vol. 3, No. 10, pp. 1587-1590, 2001.
Chem Abstract Database Acession No. 1985-62152.
Doan, et al., "Virus-like particles as HIV-1 vaccines," Rec. Med. Virol. vol. 15, pp. 75-88, 2005.
Hadden, et al., "Pyrimidine dimer excision in a *Bacillus subtilis* Uvr-mutant," Journal of Bacteriology, vol. 139, No. 1, pp. 247-255, 1979.
Latham, et al., Formation of Wild-Type and Chimeric Influenza Virus-Like Particles following Simultaneous Expression of Only Four Structural Proteins, Journal of Virology, vol. 75, No. 13, pp. 6154-6165, 2001.
Nahrstedt, et al., Structural and functional characterizationof the *Bacillus* magatarium uvrBA locus and generation of US-sensitive mutants, Appl Microbiol Biotechnol, vol. 65, pp. 193-199, 2004.
Wade, et al., "A Dihydroisoxazole-Based Route to 2,3,6-Trideoxy-3-Aminohexose Derivatives," Tetrahedron Letters, vol. 30, No. 33, pp. 5969-5972, 1989.
Waldeck, et al., "Targeted deletion of the uvrBA operon and biological containment in the industrially important *Bacillus licheniformis*," Appl Microbiol Biotechnol, vol. 73, pp. 1340-1347, 2007.

* cited by examiner

*Primary Examiner* — David K O Dell
(74) *Attorney, Agent, or Firm* — Susan L. Hess; Henry Jeanette; John C. Todaro

(57) ABSTRACT

In its many embodiments, the present invention provides a novel class of heterocyclic compounds as modulators of gamma secretase, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the central nervous system using such compounds or pharmaceutical compositions.

11 Claims, No Drawings

GAMMA SECRETASE MODULATORS

REFERENCE TO RELATED APPLICATION

This application claims the benefit of U.S. Provisional Application No. 60/941,396 filed Jun. 1, 2007.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as A$\beta$) production which is effective in the treatment of diseases caused by A$\beta$ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

A$\beta$ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of A$\beta$ protein are A$\beta$40 consisting of 40 amino acids and A$\beta$42 having two additional amino acids at the C-terminal. The A$\beta$40 and A$\beta$42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is observed in familial Alzheimer's disease, increase production of A$\beta$40 and A$\beta$42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of A$\beta$40 and A$\beta$42 are expected as an agent for controlling progress of Alzheimer's disease or for preventing the disease.

These A$\beta$3s are produced when APP is cleaved by beta secretase and subsequently clipped by gamma secretase. In consideration of this, creation of inhibitors of $\gamma$ secretase and $\beta$ secretase has been attempted for the purpose of reducing production of A$\beta$s. Many of these secretase inhibitors already known are peptides or peptidomimetics such as L-685,458. L-685,458, an aspartyl protease transition stale mimic, is a potent inhibitor of amyloid $\beta$-protein precursor $\gamma$-secretase activity, Biochemistry, Aug. 1, 2000, 39(30), p. 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingelheim, published Nov. 24, 2005); WO 2006/045554 (Cellzone AG, published May 4, 2006); WO 2004/110350 (Neurogenetics, published Dec. 23, 2004); WO 2004/071431 (Myriad Genetics, published Aug. 26, 2004); US 2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with A$\beta$. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the A$\beta$ using such compounds or pharmaceutical compositions.

The compounds of this invention (Formula I) can be useful as gamma secretase modulators and can be useful in the treatment and prevention of diseases such as, for example, Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), Olfactory function loss (Getchell, et.al. Neurobiology of Aging, 663-673, 24, 2003).

In one embodiment, the present application discloses a compound, or pharmaceutically acceptable salts, solvates, esters or prodrugs of said compound, said compound having the general structure shown in Formula I:

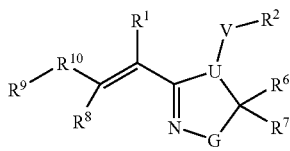

Formula I wherein $R^1, R^2, R^6, R^7, R^8, R^9, R^{10}$, G, U and V are as defined below.

In one embodiment, the present application discloses a compound, or pharmaceutically acceptable salts, solvates, esters or prodrugs of said compound, said compound having the general structure shown in Formula I:

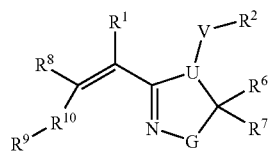

Formula IA wherein $R^1, R^2, R^6, R^7, R^8, R^9, R^{10}$, G, U and V are as defined below.

The compounds of Formula I can be useful as gamma secretase modulators and can be useful in the treatment and prevention of diseases such as, for example, central nervous system disorders such as Alzheimers disease and Downs Syndrome.

This invention also provides compounds of formula I.

This invention also provides pharmaceutically acceptable salts of the compounds of formula I.

This invention also provides pharmaceutically acceptable esters of the compounds of formula I.

This invention also provides pharmaceutically solvates of the compounds of formula I.

This invention also provides compounds of formula I in pure and isolated form.

This invention also provides compounds of formula I in pure form.

This invention also provides compounds of formula I in isolated form.

This invention also provides compounds 1A to 42A.

This invention also provides compounds 1 to 7 and 9 to 22.

This invention also provides compounds 1 to 7 and 9.

This invention also provides compounds 10 to 22.

This invention also provides pharmaceutical compositions comprising an effective amount of one or more (e.g., one) compounds of formula I, or a pharmaceutically acceptable salt, ester or solvate thereof, and a pharmaceutically acceptable carrier.

This invention also provides pharmaceutical compositions comprising an effective amount of one or more (e.g., one) compounds of formula I, or a pharmaceutically acceptable salt, ester or solvate thereof, and an effective amount of one or more (e.g., one) other pharmaceutically active ingredients (e.g., drugs), and a pharmaceutically acceptable carrier.

This invention also provides a method for modulating (including inhibiting, antagonizing and the like) gamma-secretase, comprising administering an effective (i.e., therapeutically effective) amount of one or more compounds of formula I to a patient in need of treatment.

This invention also provides a method for modulating (including inhibiting, antagonizing and the like) gamma-secretase, comprising administering an effective (i.e., therapeutically effective) amount of a compound of formula I to a patient in need of treatment.

This invention also provides a method of treating one or more neurodegenerative diseases, comprising administering an effective (i.e., therapeutically effective) amount of one or more compounds of formula I to a patient in need of treatment.

This invention also provides a method of treating one or more neurodegenerative diseases, comprising administering an effective (i.e., therapeutically effective) amount of a compound of formula I to a patient in need of treatment.

This invention also provides a method of inhibiting the deposition of amyloid protein (e.g., amyloid beta protein) in, on or around neurological tissue (e.g., the brain), comprising administering an effective (i.e., therapeutically effective) amount of one or more compounds of formula I to a patient in need of treatment.

This invention also provides a method of inhibiting the deposition of amyloid protein (e.g., amyloid beta protein) in, on or around neurological tissue (e.g., the brain), comprising administering an effective (i.e., therapeutically effective) amount of a compound of formula I to a patient in need of treatment.

This invention also provides a method of treating Alzheimer's disease, comprising administering an effective (i.e., therapeutically effective) amount of one or more compounds of formula I to a patient in need of treatment.

This invention also provides a method of treating Alzheimer's disease, comprising administering an effective (i.e., therapeutically effective) amount of a compound of formula I to a patient in need of treatment.

This invention also provides a method of treating Alzheimer's disease, comprising administering an effective (i.e., therapeutically effective) amount of one or more compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Alzheimer's disease, comprising administering an effective (i.e., therapeutically effective) amount of one or more compounds of formula I, in combination with an effective (i.e., therapeutically effective) amount of one or more compounds selected from the group consisting of Aβ antibody inhibitors, gamma secretase inhibitors and beta secretase inhibitors.

This invention also provides combinations comprising an effective (i.e., therapeutically effective) amount of one or more compounds of formula I, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors.

This invention also provides a method of treating Alzheimer's disease, comprising administering an effective (i.e., therapeutically effective) amount of a compound of formula I, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective (i.e., therapeutically effective) amount of one or more compounds of formula I to a patient in need of treatment.

This invention also provides a method of treating Downs syndrome, comprising administering an effective (i.e., therapeutically effective) amount of a compound of formula I to a patient in need of treatment.

This invention also provides a method of treating Downs syndrome, comprising administering an effective (i.e., therapeutically effective) amount of one or more compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective (i.e., therapeutically effective) amount of a compound of formula I, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs).

This invention also provides a method of treating mild cognitive impairment, comprising administering an effective amount of one or more (e.g., one) compounds of formula I to a patient in need of treatment.

This invention also provides a method of treating glaucoma, comprising administering an effective amount of one or more (e.g., one) compounds of formula I to a patient in need of treatment.

This invention also provides a method of treating cerebral amyloid angiopathy, comprising administering an effective amount of one or more (e.g., one) compounds of formula I to a patient in need of treatment.

This invention also provides a method of treating stroke, comprising administering an effective amount of one or more (e.g., one) compounds of formula I to a patient in need of treatment.

This invention also provides a method of treating dementia, comprising administering an effective amount of one or more (e.g., one) compounds of formula I to a patient in need of treatment.

This invention also provides a method of treating microgliosis, comprising administering an effective amount of one or more (e.g., one) compounds of formula I to a patient in need of treatment.

This invention also provides a method of treating brain inflammation, comprising administering an effective amount of one or more (e.g., one) compounds of formula I to a patient in need of treatment.

This invention also provides a method of treating olfactory function loss, comprising administering an effective amount of one or more (e.g., one) compounds of formula I to a patient in need of treatment.

This invention also provides pharmaceutical compositions comprising a combination of an effective amount of one or more (e.g., one) compounds of formula I, in combination with an effective amount of one or more compounds selected from the group consisting of cholinesterase inhibitors, Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient, the combined quantities of the compound of formula I and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described below), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides any one of the methods disclosed above and below wherein the compound is selected from the group consisting of the compounds 1 to 7 and 9 to 22 (see Table 1).

This invention also provides any one of the methods disclosed above and below wherein the compound of formula I is selected from the group consisting of the compounds 1A to 40A.

This invention also provides any one of the pharmaceutical compositions disclosed above and below wherein the compound is selected from the group consisting of the compounds 1 to 7 and 9 to 22.

This invention also provides any one of the pharmaceutical compositions disclosed above and below wherein the compound is any one of the compounds 1A to 40A.

Other embodiments of this invention are directed to any one of the embodiments above or below that are directed to formula I, or the use of formula I (e.g. the embodiments directed to methods of treatment, pharmaceutical compositions and kits), wherein the compound is a compound of formula IA instead of formula I. Those skilled in the art will appreciate that the compounds of formula I and formula IA are isomers of each other.

DETAILED DESCRIPTION

In one embodiment, the present invention discloses compounds which are represented by structural Formula I, or a pharmaceutically acceptable salt, solvate, ester or prodrug thereof, wherein the various moieties are described below.

For the compounds of formula I and IA, $R^1$, $R^2$, $R^8$, $R^7$, $R^8$, $R^9$, $R^{10}$, G, U and V are each independently selected.

Thus, in one embodiment; the present invention discloses compounds which are represented by structural Formula I:

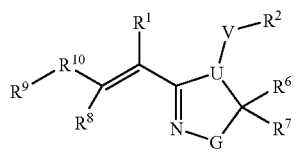

Formula I or a pharmaceutically acceptable salt, solvate, ester or prodrug thereof, wherein:
either (i) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;
or (ii) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;
and $R^6$ and $R^7$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;
and
U is

or N;
G is O or S;
V is selected from the group consisting of a bond, O, —C(O)—, and N($R^{14}$);
$R^1$, $R^5$ and $R^7$ (when $R^7$ is not joined to $R^6$) can be the same or different, each being independently selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;
or, alternatively, $R^1$ and $R^8$ are taken together to form a bond (i.e., there is a triple bond between the carbon atom to which $R^1$ was bonded to and the carbon to which $R^8$ was bonded to, i.e., the compound of formula I is a compound of formula II:

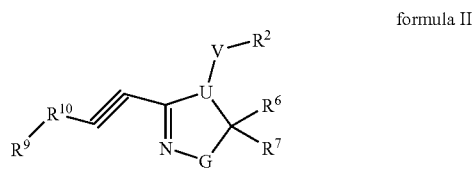

formula II and $R^5$ and $R^7$ are as defined above);
$R^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$);
$R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;
$R^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocycylylalkyl- and the moieties:

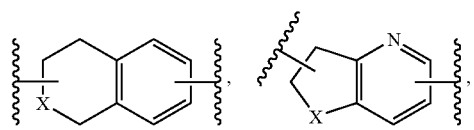

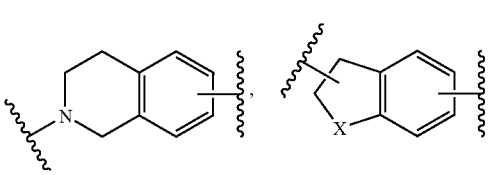

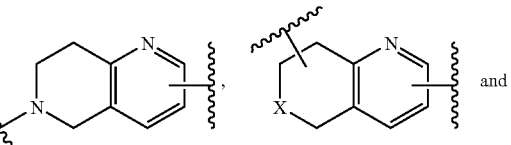

and

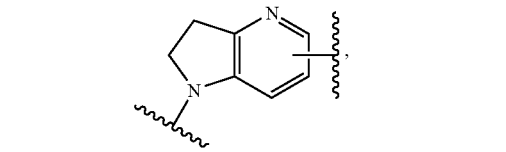

where X is O, N($R^{14}$) or S;
wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl-heterocyclylalkyl- for $R^{10}$ as well as the above-noted moieties for $R^{10}$ can be unsubstituted or optionally independently substituted with 1-3 substituents which can be the same or different, each being independently selected from the group consisting of the moieties shown below; and $R^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, $R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $R^{18}$-alkyl, $R^{18}$-cycloalkyl, $R^{18}$-cycloalkylalkyl, $R^{18}$-heterocyclyl, $R^{18}$-heterocyclylalkyl, $R^{18}$-aryl, $R^{18}$-arylalkyl, $R^{18}$-heteroaryl and $R^{18}$-heteroarylalkyl;

$R^{18}$ is 1-5 substituents independently selected from the group consisting of alkyl, alkenyl, alkynyl, aryl, arylalkyl, arylalkenyl, arylalkynyl, —$NO_2$, halo, heteroaryl, HO-alkyoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$_2R^{20}$, —S(O)$NH_2$, —S(O)NH(alkyl), —S(O)N(alkyl)(alkyl), —S(O)NH(aryl), —S(O)$_2NH_2$, —S(O)$_2$NH$R^{19}$, —S(O)$_2$NH(heterocyclyl), —S(O)$_2$N(alkyl)$_2$, —S(O)$_2$N(alkyl)(aryl), —O$CF_3$, —OH, —O$R^{20}$, —O-heterocyclyl, —O-cycloalkylalkyl, —O-heterocyclylalkyl, —$NH_2$, —NH$R^{20}$, —N(alkyl)$_2$, —N(arylalkyl)$_2$, —N(arylalkyl)-(heteroarylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two $R^{18}$ moieties on adjacent carbons can be linked together to form:

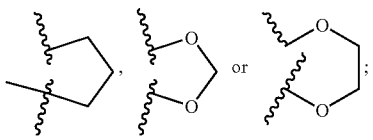

$R^{19}$ is alkyl, cycloalkyl, aryl, arylalkyl or heteroarylalkyl;
$R^{20}$ is alkyl, cycloalkyl, aryl, halo substituted aryl, arylalkyl, heteroaryl or heteroarylalkyl;

wherein each of the alkyl, cycloalkyl, cycloalkenyl, cycloalkylalkyl, heterocyclyl, heterocyclylalkyl, aryl, arylalkyl, heteroaryl, heteroarylalkyl, alkenyl and alkynyl groups in $R^1$, $R^2$-$R^6$, $R^5$, $R^7$, $R^8$, $R^9$, $R^{10}$ and $R^{14}$ is independent unsubstituted or optionally substituted by 1 to 5 $R^{21}$ groups independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl—N($R^{15}$)($R^{16}$), —N($R^{15}$)C(O)$R^{16}$, —$CH_2$—N($R^{15}$)C(O)$R^{16}$, —$CH_2$—N($R^{15}$)C(O)N($R^{16}$)($R^{17}$), —$CH_2R^{15}$, —$CH_2$N($R^{15}$)($R^{16}$), —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, =NO$R^{15}$, —$N_3$, —$NO_2$ and —S(O)$_2R^{15}$;

wherein each of the alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —$CF_3$, —CN, —O$R^{15}$, —C(O)$R^{15}$, —C(O)O$R^{15}$, -alkyl—C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$^2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —$N_3$, =NO$R^{15}$, —$NO_2$, —S(O)$R^{15}$ and —S(O)$_2R^{15}$.

The statement above: "either (i) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; or (ii) $R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and $R^6$ and $R^7$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;" means that the occurrences of (i) and (ii) are mutually exclusive and that only one of (i) and (ii) can be present at any given time.

It should be understood that when $R^2$ and $R^6$ are joined together to form a C4-C8 cycloalkyl, C4-C8 cycloalkenyl, 5-8 membered heterocyclyl or 5-8 membered heterocyclenyl moiety, each of said cycloalkyl, cycloalkenyl, heterocyclyl or heterocyclenyl moiety independently may optionally additionally be fused with an aryl or heteroaryl ring, wherein the ring moiety resulting from the fusion may be unsubstituted or optionally independently substituted with 1-5 substituents which can be the same or different, each substituent being independently selected from the group consisting of the moieties shown above.

It should also be understood that when $R^6$ and $R^7$ are joined together to form a C4-C8 cycloalkyl, C4-C8 cycloalkenyl, 5-8 membered heterocyclyl or 5-8 membered heterocyclenyl moiety, each of said cycloalkyl, cycloalkenyl, heterocyclyl or heterocyclenyl moiety independently may optionally additionally be fused with an aryl or heteroaryl ring, wherein the ring moiety resulting from the fusion may be unsubstituted or optionally independently substituted with 1-5 substituents which can be the same or different, each substituent being independently selected from the group consisting of the moieties shown above.

In another embodiment of this invention, each of the alkyl, cycloalkyl, cycloalkylalkyl, heterocyclyl, heterocyclylalkyl, aryl, arylalkyl, heteroaryl, heteroarylalkyl, alkenyl and alkynyl groups in $R^1$, $R^2$-$R^6$, $R^5$, $R^7$, $R^8$, $R^9$, $R^{10}$ and $R^{14}$ is independently unsubstituted or optionally substituted by 1 to 5 $R^{21}$ groups independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15}S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$; wherein each of the alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl groups in $R^{21}$ is independently unsubstituted or substituted by 1 to 5 $R^{22}$ groups independently selected from the group consisting of alkyl, cycloalkyl, cycloalkenyl, heterocyclyl, aryl, heteroaryl, halo, —$CF_3$, —CN, —$OR^{15}$, —$C(O)R^{15}$, —$C(O)OR^{15}$, -alkyl-$C(O)OR^{15}$, $C(O)N(R^{15})(R^{16})$, —$SR^{15}$, —$S(O)N(R^{15})(R^{16})$, —$S(O)_2N(R_{15})(R_{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, =$NOR^{15}$, —$NO_2$, —$S(O)R^{15}$ and —$S(O)_2R^{15}$.

Thus, in one embodiment, the present invention discloses compounds which are represented by structural Formula I:

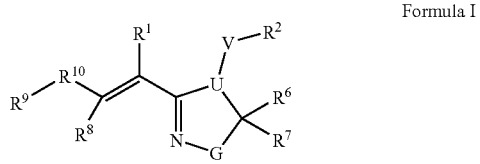

Formula I or a pharmaceutically acceptable salt, solvate, ester or prodrug thereof, wherein:
either:
(i) $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; or (ii)
(a) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and (b) $R^6$ and $R^7$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and (c) said $R^6$ and $R^7$ cycloalkyl, cycloalkenyl, heterocyclyl or heterocyclenyl moiety is optionally fused with an aryl or heteroaryl ring, and the ring moiety resulting from the fusion is optionally substituted with 1-5 independently selected $R^{21}$ substituents; and U is

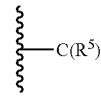

or N;

G is O or S;

V is selected from the group consisting of a bond, O, —C(O)—, and $N(R^{14})$;

$R^1$, $R^5$ and $R^7$ (when $R^7$ is not joined to $R^6$) are each being independently selected from the group consisting of: H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1-5 independently selected $R^{21}$ substituents;

or, alternatively, $R^1$ and $R^8$ are taken together to form a bond (i.e., there is a triple bond between the carbon atom to which $R^1$ was bonded to and the carbon to which $R^8$ was bonded to, i.e., the compound of formula I is a compound of formula II:

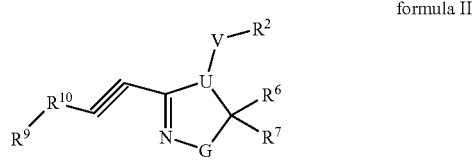

formula II and $R^5$ and $R^7$ are as defined above);

$R^8$ is selected from the group consisting of: H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being optionally substituted with 1-3 independently selected $R^{21}$ substituents;

$R^9$ is selected from the group consisting of: alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said $R^9$ substituents is optionally substituted with 1-3 independently selected $R^{21}$ substituents;

$R^{10}$ is selected from the group consisting of: a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

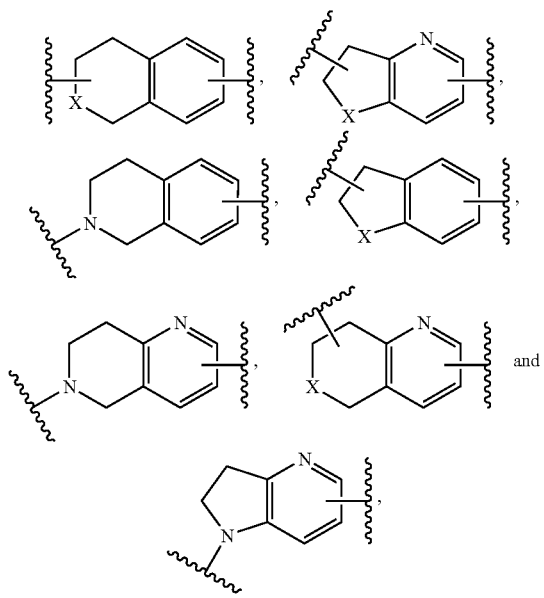

wherein X is O, $N(R^{14})$ or S; and wherein each of said $R^{10}$ moieties (except for the bond) is optionally substituted with 1-3 independently selected $R^{21}$ substituents;

$R^9$ is selected from the group consisting of: alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said $R^9$ substituents is optionally substituted with 1-3 independently selected $R^{21}$ substituents;

$R^{14}$ is selected from the group consisting of: H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$), wherein each alkyl, alkenyl, alkynyl, cycloalkyl, cycloalkylalkyl, cycloalkenyl, heterocyclyl, heterocyclylalkyl, aryl, arylalkyl, heteroaryl, and heteroarylalkyl moiety is optionally substituted with 1-5 independently selected $R^{21}$ substitutents;

$R^{15}$, $R^{16}$ and $R^{17}$ are independently selected from the group consisting of: H, alkyl, alkenyl, alkynyl, cycloalkyl, cycloalkylalkyl-, heterocyclyl, heterocyclylalkyl-, aryl, arylalkyl-, heteroaryl, heteroarylalkyl-, arylcycloalkyl-, arylheterocyclyl-, $(R^{18})_r$-alkyl, $(R^{18})_r$-cycloalkyl, $(R^{18})_r$-cycloalkylalkyl-, $(R^{18})_r$-heterocyclyl-, $(R^{18})_r$-heterocyclylalkyl-, $(R^{18})_r$-aryl, $(R^{18})_r$-arylalkyl-, $(R^{18})_r$-heteroaryl- and $(R^{18})_r$-heteroarylalkyl-, wherein each r is independently 1 to 5;

Each $R^{18}$ is independently selected from the group consisting of: alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)$R^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two $R^{18}$ moieties on adjacent carbons can be linked together to form:

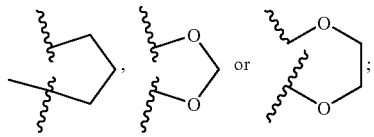

$R^{19}$ is selected from the group consisting of: alkyl, cycloalkyl, aryl, arylalkyl and heteroarylalkyl;

$R^{20}$ is selected from the group consisting of: alkyl, cycloalkyl, aryl, halo substituted aryl, arylalkyl-, heteroaryl and heteroarylalkyl-;

Each $R^{21}$ independently selected from the group consisting of: alkyl, alkenyl, alkynyl, cycloalkyl, cycloalkylalkyl-, cycloalkenyl, heterocyclyl, heterocyclylalkyl-, aryl, arylalkyl-, heteroaryl, heteroarylalkyl-, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$;

Wherein each of the alkyl, cycloalkenyl, cycloalkyl, cycloalkylalkyl-, heterocyclyl, heterocyclylalkyl, aryl, arylalkyl-, heteroaryl, heteroarylalkyl-, alkenyl and alkynyl groups in $R^{21}$ is optionally substituted with 1 to 5 $R^{22}$ groups; and Each $R^{22}$ is independently selected from the group consisting of: alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$.

In another embodiment, the present application discloses a compound, or pharmaceutically acceptable salts, solvates, esters or prodrugs of said compound, said compound having the general structure shown in Formula I:

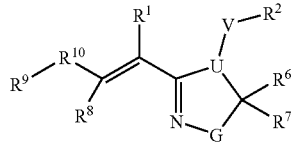

Formula I wherein:

$R^2$ and $R^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;

U is

or N;

G is O or S;

V is selected from the group consisting of a bond, O, —C(O)—, and $N(R^{14})$;

$R^1$, $R^5$ and $R^7$ can be the same or different, each being independently selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

$R^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$);

$R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

$R^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

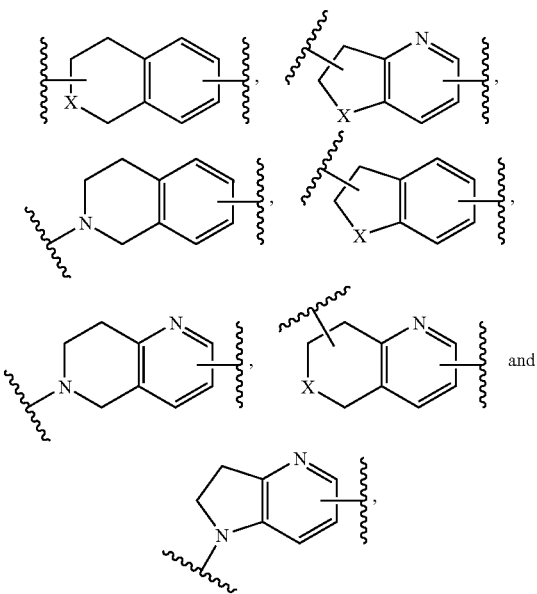

where X is O, $N(R^{14})$ or S;

wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- heterocyclylalkyl- for $R^{10}$ as well as the above-noted moieties for $R^{10}$ can be unsubstituted or optionally independently substituted with 1-3 substituents which can be the same or different, each being independently selected from the group consisting of the moieties shown below; and $R^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below, $R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $R^{18}$-alkyl, $R^{18}$-cycloalkyl, $R^{18}$-cycloalkylalkyl, $R^{18}$-heterocyclyl, $R^{18}$-heterocyclylalkyl, $R^{18}$-aryl, $R^{18}$-arylalkyl, $R^{18}$-heteroaryl and $R^{18}$-heteroarylalkyl;

$R^{18}$ is 1-5 substituents independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)$R^{19}$, —C(O)OH, C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2R^{20}$, —S(O)NH$_2$, —S(O)NH (alkyl), —S(O)N(alkyl)(alkyl), —S(O)NH(aryl), —S(O)$_2$NH$_2$, —S(O)$_2$NH$R^{19}$, —S(O)$_2$NH(heterocyclyl), —S(O)$_2$N(alkyl)$_2$, —S(O)$_2$N(alkyl)(aryl), —OCF$_3$, —OH, —O$R^{20}$, —O-heterocyclyl, —O-cycloalkylalkyl, —O-heterocyclylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternatively, two R$^{18}$ moieties on adjacent carbons can be linked together to form:

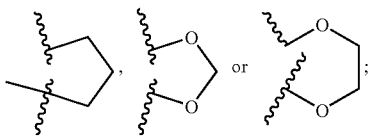

R$^{19}$ is alkyl, cycloalkyl, aryl, arylalkyl or heteroarylalkyl;

R$^{20}$ is alkyl, cycloalkyl, aryl, halo substituted aryl, arylalkyl, heteroaryl or heteroarylalkyl;

wherein each of the alkyl, cycloalkyl, cycloalkenyl cycloalkylalkyl, heterocyclyl, heterocyclylalkyl, aryl, arylalkyl, heteroaryl, heteroarylalkyl, alkenyl and alkynyl groups in R$^1$, R$^2$-R$^6$, R$^5$, R$^7$, R$^8$, R$^9$, R$^{10}$ and R$^{14}$ is independently unsubstituted or optionally substituted by 1 to 5 R$^{21}$ groups independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$; and wherein each of the alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl groups in R$^{21}$ is independently unsubstituted or substituted by 1 to 5 R$^{22}$ groups independently selected from the group consisting of alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$.

In another embodiment, the present application discloses a compound, or pharmaceutically acceptable salts, solvates, esters or prodrugs of said compound, said compound having the general structure shown in Formula I:

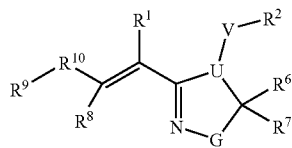

Formula I wherein:

R$^2$ and R$^6$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below; and R$^6$ and R$^7$ are joined together to form a C4-C8 cycloalkyl, C4-C8 cycloalkenyl, 5-8 membered heterocyclyl or 5-8 membered heterocyclenyl moiety, with each of said cycloalkyl or heterocyclyl moiety being unsubstituted or optionally independently being substituted with 1-5 substituents which can be the same or different, each substituent being independently selected from the group consisting of the moieties shown below;

and

U is

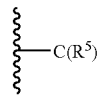

or N;

G is O or S;

V is selected from the group consisting of a bond, O, —C(O)—, and N(R$^{14}$);

R$^1$, R$^5$ and R$^7$ (when R$^7$ is not joined to R$^6$) can be the same or different, each being independently selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

R$^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$);

R$^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents which can be the same or different, each substituent being independently selected from the group consisting of the moieties shown below;

R$^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl- and the moieties:

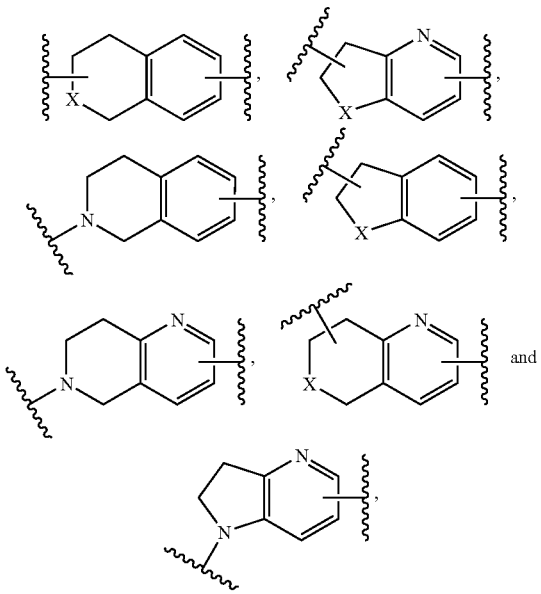

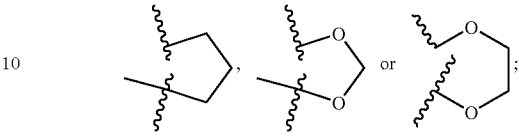

where X is O, N(R$^{14}$) or S;

wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- heterocyclylalkyl- for R$^{10}$ as well as the above-noted moieties for R$^{10}$ can be unsubstituted or optionally independently substituted with 1-3 substituents which can be the same or different, each being independently selected from the group consisting of the moieties shown below; and R$^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-3 substituents which can be the same or different, each substituent being independently selected from the group consisting of the moieties shown below;

R$^{15}$, R$^{16}$ and R$^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, R$^{18}$-alkyl, R$^{18}$-cycloalkyl, R$^{18}$-cycloalkylalkyl, R$^{18}$-heterocyclyl, R$^{18}$-heterocyclylalkyl, R$^{18}$-aryl, R$^{18}$-arylalkyl, R$^{18}$-heteroaryl and R$^{18}$-heteroarylalkyl;

R$^{18}$ is 1-5 substituents independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, alternately, two R$^{18}$ moieties on adjacent carbons can be linked together to form:

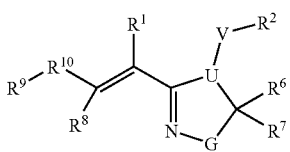

R$^{19}$ is alkyl, cycloalkyl, aryl, arylalkyl or heteroarylalkyl;

R$^{20}$ is alkyl, cycloalkyl, aryl, halo substituted aryl, arylalkyl, heteroaryl or heteroarylalkyl;

wherein each of the alkyl, cycloalkyl, cycloalkenyl, cycloalkenyl, cycloalkylalkyl, heterocyclyl, heterocyclylalkyl, aryl, arylalkyl, heteroaryl, heteroarylalkyl, alkenyl and alkynyl groups in R$^1$, R$^2$-R$^6$, R$^5$, R$^7$, R$^8$, R$^9$, R$^{19}$ and R$^{14}$ is independently unsubstituted or optionally substituted by 1 to 5 R$^{21}$ groups independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^1$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$^2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, =NOR$^{15}$, —N$_3$, —NO$_2$ and —S(O)$_2$R$^{15}$; and wherein each of the alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl groups in R$^{21}$ is independently unsubstituted or substituted by 1 to 5 R$^{22}$ groups independently selected from the group consisting of alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$.

In another embodiment, the present application discloses a compound, or pharmaceutically acceptable salts, solvates, esters or prodrugs of said compound, said compound having the general structure shown in Formula I:

wherein:

U is

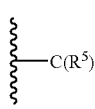

or N;

G is O or S;

V is selected from the group consisting of a bond, O, —C(O)—, and N(R$^{19}$);

R$^1$, R$^5$ and R$^7$ can be the same or different, each being independently selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of the moieties shown below;

R$^2$ and R$^6$ are joined together to form a C4-C8 cycloalkyl or a 5-8 membered heterocyclyl moiety, with each of said cycloalkyl or heterocyclyl moiety being unsubstituted or optionally independently being substituted with 1-5 substituents which can be the same or different, each substituent being independently selected from the group consisting of the moieties shown below;

R$^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$);

R$^8$ is selected from the group consisting of H, alkyl, cycloalkyl, aryl and heteroaryl, with each of said alkyl, cycloalkyl, aryl and heteroaryl being unsubstituted or optionally independently substituted with 1-3 substituents which can be the same or different, each substituent being independently selected from the group consisting of halo, alkyl, —CN, —NH$_2$, —NH(alkyl), —N(alkyl)$_2$, hydroxy and alkoxy groups;

R$^{10}$ is selected from the group consisting of a bond, aryl, heteroaryl, cycloalkyl, heterocyclyl, arylalkyl, alkylaryl, heteroarylalkyl, heterocyclylalkyl and the moieties:

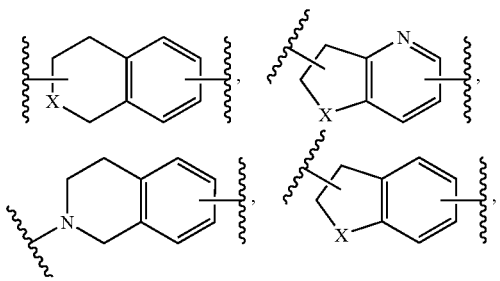

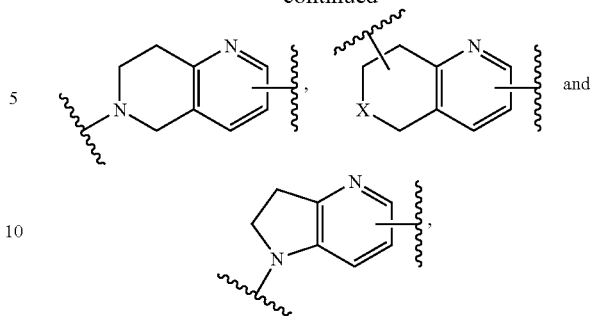

where X is O, NH or S;

wherein each of said aryl, heteroaryl, cycloalkyl, heterocyclyl and the above-noted moieties for R$^{10}$ can be unsubstituted or optionally independently substituted with 1-3 substituents which can be the same or different, each being independently selected from the group consisting of halo, alkyl, —CN, —NH$_2$, —NH(alkyl), —N(alkyl)$_2$, hydroxy and alkoxy groups; and R$^9$ is selected from the group consisting of alkyl, aryl, heteroaryl, heterocyclyl, arylalkyl, alkylaryl, heteroarylalkyl and heterocyclylalkyl wherein each of said alkyl, aryl, heteroaryl and heterocyclyl can be unsubstituted or optionally independently substituted with 1-3 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment of this invention R$^2$ and R$^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is optionally fused with an aryl or heteroaryl ring, and the ring moiety resulting from the fusion is optionally substituted with 1-5 independently selected R$^{21}$ substituents.

In another embodiment of this invention R$^2$ and R$^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is fused with an aryl or heteroaryl ring, and the ring moiety resulting from the fusion is optionally substituted with 1-5 independently selected R$^{21}$ substituents.

In another embodiment of this invention R$^2$ and R$^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected R$^{21}$ substituents, (b) said heterocyclyl moiety is optionally substituted with 1-5 independently selected R$^{21}$ substituents, and (c) said cycloalkyl, cycloalkenyl, heterocyclyl or heterocyclenyl moiety is fused with an aryl ring, and the ring moiety resulting from the fusion is optionally substituted with 1-5 independently selected R$^{21}$ substituents.

In another embodiment of this invention $R^2$ and $R^6$ are joined together to form a C4-C8 cycloalkyl, C4-C8 cycloalkenyl, 5-8 membered heterocyclyl or 5-8 membered heterocyclenyl moiety, wherein: (a) said cycloalkyl moiety is optionally substituted with 1-5 independently selected $R^{21}$ substituents, (b) said heterocyclyl moiety is optionally substituted with 1-5 independently selected $R^{21}$ substituents, and (c) said cycloalkyl, cycloalkenyl, heterocyclyl or heterocyclenyl moiety is fused with a phenyl ring, and the ring moiety resulting from the fusion is optionally substituted with 1-5 independently selected $R^{21}$ substituents.

In another embodiment of this invention:

(a) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and (b) $R^6$ and $R^7$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and (c) said $R^6$ and $R^7$ cycloalkyl, cycloalkenyl, heterocyclyl or heterocyclenyl moiety is fused with an aryl or heteroaryl ring, and the ring moiety resulting from the fusion is optionally substituted with 1-5 independently selected $R^{21}$ substituents.

In another embodiment of this invention:

(a) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and (b) $R^6$ and $R^7$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and (c) said $R^6$ and $R^7$ cycloalkyl, cycloalkenyl, heterocyclyl or heterocyclenyl moiety is fused with an aryl ring, and the ring moiety resulting from the fusion is optionally substituted with 1-5 independently selected $R^{21}$ substituents.

In another embodiment of this invention:

(a) $R^2$ and $R^6$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents, and (b) $R^6$ and $R^7$ are joined together to form a C4-C8 cycloalkyl, C4-C8 cycloalkenyl, 5-8 membered heterocyclyl or 5-8 membered heterocyclenyl moiety, wherein: (1) said cycloalkyl moiety is optionally substituted with 1-5 independently selected $R^{21}$ substituents, and (2) said heterocyclyl moiety is optionally substituted with 1-5 independently selected $R^{21}$ substituents; and (c) said $R^6$ and $R^7$ cycloalkyl, cycloalkenyl, heterocyclyl or heterocyclenyl moiety is fused with a phenyl ring, and the ring moiety resulting from the fusion is optionally substituted with 1-5 independently selected $R^{21}$ substituents.

In another embodiment, V is selected from the group consisting of a bond, O, and $N(R^{14})$.

In another embodiment of this invention $R^1$ and $R^8$ are taken together to form a bond (i.e., there is a triple bond between the carbon atom to which $R^1$ was bonded to and the carbon to which $R^8$ was bonded to, i.e., the compound of formula I is a compound of formula II:

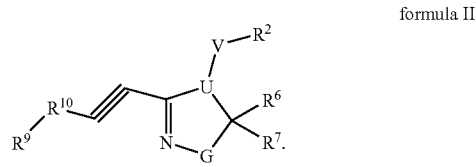

formula II

In another embodiment of this invention:

$R^1$ is selected from the group consisting of: H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents as described for $R^1$ in formula I; and $R^8$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, with each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- being unsubstituted or optionally independently substituted with 1-3 substituents, as described for $R^8$ in formula I.

Those skilled in the art will appreciate that for the compounds of the invention:

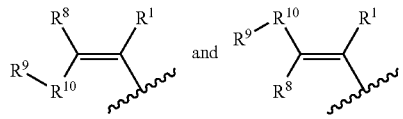

are isomers

In another embodiment, U is $C(R^5)$.

In another embodiment U is $C(R^5)$ and $R^5$ is H.

In another embodiment, U is N.

In another embodiment, G is O.

In another embodiment, G is S.

In another embodiment V is a bond.

In another embodiment V is —O—.

In another embodiment V is —$N(R^{14})$—.

In another embodiment V is —C(O)—.

In another embodiment, $R^1$ is H.

In another embodiment, $R^1$ is alkyl.

In another embodiment, $R^1$ is methyl.

In another embodiment, $R^2$ and $R^6$ are joined together to form a cyclopentyl ring.

In another embodiment, $R^2$ and $R^6$ are joined together to form a cyclopentyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a cyclohexyl ring.

In another embodiment, R$^2$ and R$^6$ are joined together to form a cyclohexyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, G is O, and R$^2$ and R$^6$ are joined together to form a piperidinyl ring including the N of U as the nitrogen of said piperidinyl ring, which is unsubstituted.

In another embodiment, U is N, G is O, and R$^2$ and R$^6$ are joined together to form a piperidinyl ring including the N of U as the nitrogen of said piperidinyl ring, wherein said piperidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, G is O, and R$^2$ and R$^6$ are joined together to form a pyrrolidinyl ring including the N of U as the nitrogen of said pyrrolidinyl ring, which is unsubstituted.

In another embodiment, U is N, G is O, and R$^2$ and R$^6$ are joined together to form a pyrrolidinyl ring including the N of U as the nitrogen of said pyrrolidinyl ring, wherein said pyrrolidinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, U is N, G is O, and R$^2$ and R$^6$ are joined together to form a piperazinyl ring including the N of U as a nitrogen of said piperazinyl ring, which is unsubstituted.

In another embodiment, U is N, G is O, and R$^2$ and R$^6$ are joined together to form a piperazinyl ring including the N of U as a nitrogen of said piperazinyl ring, wherein said piperazinyl ring is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a morpholinyl ring which is unsubstituted.

In another embodiment, R$^2$ and R$^6$ are joined together to form a morpholinyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a pyranyl ring which is unsubstituted.

In another embodiment, R$^2$ and R$^6$ are joined together to form a pyranyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment, R$^2$ and R$^6$ are joined together to form a pyrrolidinyl ring which is unsubstituted.

In another embodiment, R$^2$ and R$^6$ are joined together to form a pyrrolidinyl ring, which is substituted with 1-3 substituents which can be the same or different, each being independently selected from the group consisting of halo, alkyl, —CN, —NH$_2$, —NH(alkyl), —N(alkyl)$_2$, hydroxy and alkoxy groups.

In another embodiment R$^2$ and R$^6$ are joined together to form a ring optionally substituted with 1 to 5 independently selected R$^{21}$ substitutents, and R$^6$ and R$^7$ are joined together to form a ring optionally substituted with 1 to 5 independently selected R$^{21}$ substitutents.

In another embodiment R$^2$ and R$^6$ are joined together to form a ring optionally substituted with 1 to 5 independently selected R$^{21}$ substitutents, and R$^6$ and R$^7$ are joined together to form a ring that is fused with an aryl or heteroaryl ring, said resulting fused ring optionally substituted with 1 to 5 independently selected R$^{21}$ substitutents.

In another embodiment R$^2$ and R$^6$ are joined together to form a ring optionally substituted with 1 to 5 independently selected R$^{21}$ substitutents, and R$^6$ and R$^7$ are joined together to form a C4-C8 cycloalkyl ring that is fused with an aryl or heteroaryl ring, said resulting fused ring optionally substituted with 1 to 5 independently selected R$^{21}$ substitutents.

In another embodiment R$^2$ and R$^6$ are joined together to form a ring optionally substituted with 1 to 5 independently selected R$^{21}$ substitutents, and R$^6$ and R$^7$ are joined together to form a C4-C8 cycloalkyl ring that is fused with an aryl ring, said resulting fused ring optionally substituted with 1 to 5 independently selected R$^{21}$ substitutents.

In another embodiment R$^2$ and R$^6$ are joined together to form a ring optionally substituted with 1 to 5 independently selected R$^{21}$ substitutents, and R$^6$ and R$^7$ are joined together to form a C4-C8 cycloalkyl ring that is fused with a phenyl ring, said resulting fused ring optionally substituted with 1 to 5 independently selected R$^{21}$ substitutents.

In another embodiment R$^2$ and R$^6$ are joined together to form a ring optionally substituted with 1 to 5 independently selected R$^{21}$ substitutents, and R$^6$ and R$^7$ are joined together to form a C4-C8 cycloalkyl ring that is fused with a phenyl ring, said resulting fused ring optionally substituted with 1 to 5 independently selected R$^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment R$^2$ and R$^6$ are joined together to form a ring optionally substituted with 1 to 5 independently selected R$^{21}$ substitutents, and R$^6$ and R$^7$ are joined together to form a cyclopentyl ring that is fused with a phenyl ring, said resulting fused ring optionally substituted with 1 to 5 independently selected R$^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment R$^2$ and R$^6$ are joined together to form a ring optionally substituted with 1 to 5 independently selected R$^{21}$ substitutents, and R$^6$ and R$^7$ are joined together to form a tetrahydopyranyl ring that is fused with a phenyl ring, said resulting fused ring optionally substituted with 1 to 5 independently selected R$^{21}$ substitutents (e.g., wherein the phenyl moiety is substituted with 1-3 halo, such as, wherein the phenyl moiety is substituted with 1 halo, such as wherein the phenyl moiety is substituted with 1-3 F, such as when the phenyl moiety is substituted with 1 F).

In another embodiment R$^2$ and R$^6$ are joined together to form a ring optionally substituted with 1 to 5 independently selected R$^{21}$ substitutents, and R$^6$ and R$^7$ are joined together to form a cyclopentyl ring that is fused with a phenyl ring, wherein said phenyl moiety is substituted with 1 F.

In another embodiment $R^2$ and $R^6$ are joined together to form a ring optionally substituted with 1 to 5 independently selected $R^{21}$ substitutents, and $R^6$ and $R^7$ are joined together to form a tetrahydopyranyl ring that is fused with a phenyl ring, wherein said phenyl moiety is substituted with 1 F.

In another embodiment $R^2$ and $R^6$ are joined together to form a heterocyclyl ring optionally substituted with 1 to 5 independently selected $R^{21}$ substitutents, and $R^6$ and $R^7$ are joined together to form a ring optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and $R^6$ and $R^7$ are joined together to form a ring that is fused with an aryl or heteroaryl ring, said resulting fused ring optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and $R^6$ and $R^7$ are joined together to form a C4-C8 cycloalkyl ring that is fused with an aryl or heteroaryl ring, said resulting fused ring optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and $R^6$ and $R^7$ are joined together to form a C4-C8 cycloalkyl ring that is fused with an aryl ring, said resulting fused ring optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and $R^6$ and $R^7$ are joined together to form a C4-C8 cycloalkyl ring that is fused with a phenyl ring, said resulting fused ring optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and $R^6$ and $R^7$ are joined together to form a C4-C8 cycloalkyl ring that is fused with a phenyl ring, said resulting fused ring optionally substituted with 1 to 5 independently selected $R^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment $R^2$ and $R^6$ are joined together to form a piperidinyl ring optionally substituted with 1 to 5 independently selected $R^{21}$ substitutents, and $R^6$ and $R^7$ are joined together to form a cyclopentyl ring that is fused with a phenyl ring, said resulting fused ring optionally substituted with 1 to 5 independently selected $R^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment $R^2$ and $R^6$ are joined together to form a piperidinyl ring optionally substituted with 1 to 5 independently selected $R^{21}$ substitutents, and $R^6$ and $R^7$ are joined together to form a tetrahydopyranyl ring that is fused with a phenyl ring, said resulting fused ring optionally substituted with 1 to 5 independently selected $R^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment $R^2$ and $R^6$ are joined together to form a piperidinyl ring optionally substituted with 1 to 5 independently selected $R^{21}$ substitutents, and $R^6$ and $R^7$ are joined together to form a cyclopentyl ring that is fused with a phenyl ring, wherein said phenyl moiety is substituted with 1 F.

In another embodiment $R^2$ and $R^6$ are joined together to form a piperidinyl ring optionally substituted with 1 to 5 independently selected $R^{21}$ substitutents, and $R^6$ and $R^7$ are joined together to form a tetrahydopyranyl ring that is fused with a phenyl ring, wherein said phenyl moiety is substituted with 1 F.

In another embodiment $R^2$ and $R^6$ are joined together to form a heterocyclyl ring, and $R^6$ and $R^7$ are joined together to form a C4-C8 cycloalkyl ring that is fused with a phenyl ring, said resulting fused ring optionally substituted with 1 to 5 independently selected $R^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment $R^2$ and $R^6$ are joined together to form a piperidinyl ring, and $R^6$ and $R^7$ are joined together to form a cyclopentyl ring that is fused with a phenyl ring, said resulting fused ring optionally substituted with 1 to 5 independently selected $R^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment $R^2$ and $R^6$ are joined together to form a piperidinyl ring, and $R^6$ and $R^7$ are joined together to form a tetrahydopyranyl ring that is fused with a phenyl ring, said resulting fused ring optionally substituted with 1 to 5 independently selected $R^{21}$ substitutents (e.g., wherein the phenyl moiety is substituted with 1-3 independently selected halos, such as, wherein the phenyl moiety is substituted with 1 halo, such as wherein the phenyl moiety is substituted with 1-3 F, such as when the phenyl moiety is substituted with 1 F).

In another embodiment $R^2$ and $R^6$ are joined together to form a piperidinyl ring, and $R^6$ and $R^7$ are joined together to form a cyclopentyl ring that is fused with a phenyl ring, wherein said phenyl moiety is substituted with 1 F.

In another embodiment $R^2$ and $R^6$ are joined together to form a piperidinyl ring, and $R^6$ and $R^7$ are joined together to form a tetrahydopyranyl ring that is fused with a phenyl ring, wherein said phenyl moiety is substituted with 1 F.

In another embodiment $R^2$ and $R^6$ are joined together to form a ring optionally substituted with 1 to 5 independently selected $R^{21}$ substitutents, and said ring is fused with an aryl or heteroaryl ring, and said resulting fused ring is optionally substituted with 1 to 5 independently selected $R^{21}$ substitutents.

In another embodiment $R^2$ and $R^6$ are joined together to form a ring optionally substituted with 1 to 5 independently selected $R^{21}$ substitutents, and said ring is fused with an aryl ring, and said resulting fused ring is optionally substituted with 1 to 5 independently selected $R^{21}$ substitutents.

In another embodiment $R^2$ and $R^6$ are joined together to form a ring optionally substituted with 1 to 5 independently selected $R^{21}$ substitutents, and said ring is fused with a phenyl ring, and said resulting fused ring is optionally substituted with 1 to 5 independently selected $R^{21}$ substitutents.

In another embodiment $R^2$ and $R^6$ are joined together to form a ring, and said ring is fused with an aryl or heteroaryl ring.

In another embodiment $R^2$ and $R^6$ are joined together to form a ring, and said ring is fused with a phenyl ring.

In another embodiment $R^2$ and $R^6$ are joined together to form a heterocyclyl ring optionally substituted with 1 to 5 independently selected $R^{21}$ substitutents, and said ring is fused with an aryl or heteroaryl ring, and said resulting fused ring is optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and said ring is fused with an aryl ring, and said resulting fused ring is optionally substituted with 1 to 5 independently selected $R^{21}$ substitutents.

In another embodiment $R^2$ and $R^6$ are joined together to form a heterocyclyl ring optionally substituted with 1 to 5 independently selected $R^{21}$ substitutents, and said ring is fused with a phenyl ring, and said resulting fused ring is optionally substituted with 1 to 5 independently selected $R^{21}$ substitutents.

In another embodiment $R^2$ and $R^6$ are joined together to form a heterocyclyl ring, and said ring is fused with an aryl or heteroaryl ring.

In another embodiment $R^2$ and $R^6$ are joined together to form a heterocyclyl ring, and said ring is fused with a phenyl ring.

In another embodiment $R^2$ and $R^6$ are joined together to form a piperidinyl ring (e.g., U is N) optionally substituted with 1 to 5 independently selected $R^{21}$ substitutents, and said ring is fused with an aryl or heteroaryl ring, and said resulting fused ring is optionally substituted with 1 to 5 independently selected $R^{21}$ substitutents.

In another embodiment $R^2$ and $R^6$ are joined together to form a piperidinyl ring (e.g., U is N) optionally substituted with 1 to 5 independently selected $R^{21}$ substitutents, and said ring is fused with an aryl ring, and said resulting fused ring is optionally substituted with 1 to 5 independently selected $R^{21}$ substitutents.

In another embodiment $R^2$ and $R^6$ are joined together to form a piperidinyl ring (e.g., U is N) optionally substituted with 1 to 5 independently selected $R^{21}$ substitutents, and said ring is fused with a phenyl ring, and said resulting fused ring is optionally substituted with 1 to 5 independently selected $R^{21}$ substitutents.

In another embodiment $R^2$ and $R^6$ are joined together to form a piperidinyl ring (e.g., U is N), and said ring is fused with an aryl or heteroaryl ring.

In another embodiment $R^2$ and $R^6$ are joined together to form a piperidinyl ring (e.g., U is N), and said ring is fused with a phenyl ring.

In another embodiment, $R^7$ is aryl.
In another embodiment, $R^7$ is an unsubstituted phenyl.
In another embodiment, $R^7$ is a phenyl which is substituted with 1-4 substituents which can be the same or different, each substituent being independently selected from the group consisting of halo, alkyl, —CN, —NH$_2$, —NH(alkyl), —N(alkyl)$_2$, hydroxy, alkoxy, aryl and heteroaryl groups.
In another embodiment, $R^7$ is 4-fluorophenyl.
In another embodiment, $R^7$ is unsubstituted naphthyl.
In another embodiment, $R^7$ is naphthyl which is substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.

In another embodiment, $R^7$ is unsubstituted biphenyl.
In another embodiment, $R^7$ is biphenyl which is substituted with 1-4 substituents which can be the same or different, each substituent being independently selected from the group consisting of halo, alkyl, —CN, —NH$_2$, —NH(alkyl), —N(alkyl)$_2$, hydroxy and alkoxy groups.
In another embodiment, $R^7$ is $R^7$ is 3-(1,1'-biphenyl)-yl.
In another embodiment, $R^7$ is $R^7$ is 4-(1,1'-biphenyl)-yl.
In another embodiment, $R^8$ is H.
In another embodiment, $R^8$ is alkyl.
In another embodiment, $R^8$ is methyl.
In another embodiment, $R^{10}$ is aryl.
In another embodiment, $R^{10}$ is phenyl.
In another embodiment, $R^{10}$ is heteroaryl.
In another embodiment $R^{10}$ is aryl substituted with 1 to 3 independently selected $R^{21}$ moieties.
In another embodiment $R^{10}$ is aryl substituted with 1 to 3 $R^{21}$ moieties, wherein each $R^{21}$ moiety is the same or different —OR$^{15}$ group.
In another embodiment $R^{10}$ is aryl substituted with 1 $R^{21}$ moiety.
In another embodiment $R^{10}$ is aryl substituted with one $R^{21}$ moiety, and said $R^{21}$ moiety is —OR$^{15}$.
In another embodiment $R^{10}$ is aryl substituted with one $R^{21}$ moiety, said $R^{21}$ moiety is —OR$^{15}$, and said $R^{15}$ is alkyl.
In another embodiment $R^{10}$ is aryl substituted with one $R^{21}$ moiety, said $R^{21}$ moiety is —OR$^{15}$, said $R^{15}$ is alkyl, and said alkyl is methyl (i.e., said $R^{21}$ moiety is —OCH$_3$).
In another embodiment $R^{10}$ is phenyl substituted with 1 to 3 independently selected $R^{21}$ moieties.
In another embodiment $R^{10}$ is phenyl substituted with 1 to 3 $R^{21}$ moieties, wherein each $R^{21}$ moiety is the same or different —OR$^{15}$ group.
In another embodiment $R^{10}$ is phenyl substituted with 1 $R^{21}$ moiety.
In another embodiment $R^{10}$ is phenyl substituted with one $R^{21}$ moiety, and said $R^{21}$ moiety is —OR$^{15}$.
In another embodiment $R^{10}$ is phenyl substituted with one $R^{21}$ moiety, said $R^{21}$ moiety is —OR$^{15}$, and said $R^{15}$ is alkyl.
In another embodiment $R^{10}$ is phenyl substituted with one $R^{21}$ moiety, said $R^{21}$ moiety is —OR$^{15}$, said $R^{15}$ is alkyl, and said alkyl is methyl (i.e., said $R^{21}$ moiety is —OCH$_3$).
In another embodiment $R^{10}$ is:

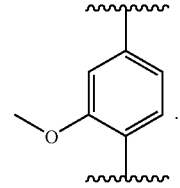 [SMILES: *c1ccc(*)c(OC)c1]

In another embodiment $R^{10}$ is:

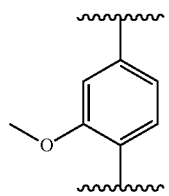 [SMILES: *c1ccc(*)c(OC)c1]

wherein the —R$^{10}$—R$^9$ moiety is:

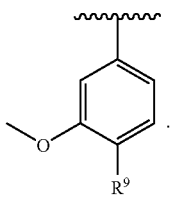

In another embodiment R$^{10}$ is aryl substituted with 1 to 3 R$^{21}$ moieties, wherein each R$^{21}$ moiety is the same or different halo.
In another embodiment R$^{10}$ is aryl substituted with 1 to 3 R$^{21}$ moieties, wherein each R$^{21}$ moiety is F.
In another embodiment R$^{10}$ is aryl substituted with one R$^{21}$ moiety, and said R$^{21}$ moiety is halo.
In another embodiment R$^{10}$ is aryl substituted with one R$^{21}$ moiety, said R$^{21}$ moiety is -halo, and said halo is F.
In another embodiment R$^{10}$ is phenyl substituted with 1 to 3 R$^{21}$ moieties, wherein each R$^{21}$ moiety is the same or different halo.
In another embodiment R$^{10}$ is phenyl substituted with 1 to 3 R$^{21}$ moieties, wherein each R$^{21}$ moiety is F.
In another embodiment R$^{10}$ is phenyl substituted with one R$^{21}$ moiety, and said R$^{21}$ moiety is halo.
In another embodiment R$^{10}$ is phenyl substituted with one R$^{21}$ moiety, said R$^{21}$ moiety is -halo, and said halo is F.
In another embodiment R$^{10}$ is:

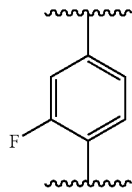 [SMILES: *c1ccc(*)c(F)c1]

In another embodiment R$^{10}$ is:

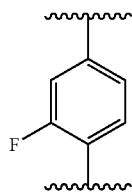

wherein the —R$^{10}$—R$^9$ moiety is:

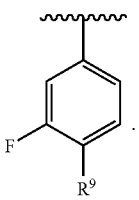

In another embodiment, R$^{10}$ is unsubstituted heteroaryl.
In another embodiment R$^{10}$ is unsubstituted heteroaryl wherein said heteroaryl is pyridyl.

In another embodiment R$^{10}$ is:

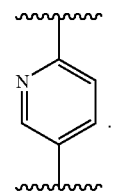

In another embodiment R$^{10}$ is:

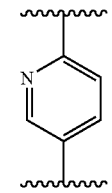 [SMILES: *c1ccc(*)nc1]

wherein the —R$^{10}$—R$^9$ moiety is:

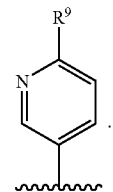

In another embodiment R$^{10}$ is selected from the group consisting of:

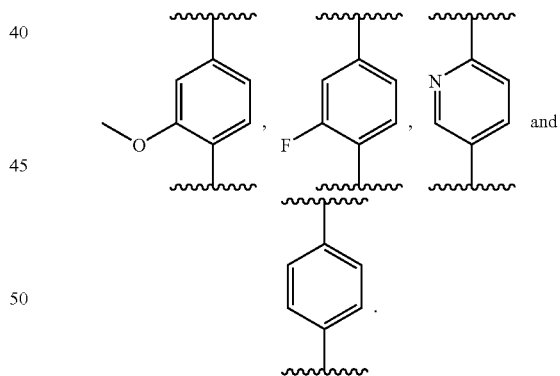

In another embodiment, R$^9$ is unsubstituted heteroaryl.
In another embodiment of this invention R$^9$ is selected from the group consisting of heteroaryl and heteroaryl substituted with 1-3 R$^{21}$ groups, and wherein each R$^{21}$ is independently selected.
In another embodiment, R$^9$ is heteroaryl which is substituted with 1-3 substituents which can be the same or different, each substituent being independently selected from the group consisting of halo, alkyl, CN, NH$_2$, NH(alkyl), N(alkyl)$_2$, hydroxyl, alkoxy, alkyl substituted with halo (e.g., alkyl substituted with F, such as, for example, —CH$_2$F), and alkyl substituted with —OR$^{15}$ (such as, for example, alkyl substituted with —OR$^{15}$ wherein R$^{15}$ is H, that is, —CH$_2$OH).

In another embodiment, R⁹ is heteroaryl which is substituted with 1-3 substituents which can be the same or different, each substituent being independently selected from the group consisting of halo, alkyl, CN, NH₂, NH(alkyl), N(alkyl)₂, hydroxy and alkoxy groups.

In another embodiment of this invention R⁹ is selected from the group consisting of imidazolyl and imidazolyl substituted with 1-3 R²¹ groups, and wherein each R²¹ is independently selected.

In another embodiment of this invention R⁹ is imidazolyl substituted with 1-3 R²¹ groups, and wherein each R²¹ is independently selected.

In another embodiment, R⁹ is imidazolyl which is substituted with 1-3 substituents which can be the same or different, each substituent being independently selected from the group consisting of halo, alkyl, CN, NH₂, NH(alkyl), N(alkyl)₂, hydroxyl, alkoxy, alkyl substituted with halo (e.g., alkyl substituted with F, such as, for example, —CH₂F), and alkyl substituted with —OR¹⁵ (such as, for example, alkyl substituted with —OR¹⁵ wherein R¹⁵ is H, that is, —CH₂OH).

In another embodiment, R⁹ is imidazolyl substituted with 1-3 substituents independently selected from the group consisting of halo, alkyl, CN, NH₂, NH(alkyl), N(alkyl)₂, hydroxy and alkoxy groups.

In another embodiment, R⁹ is imidazol-1-yl.

In another embodiment, R⁹ is 4-methyl-imidazol-1-yl.

In another embodiment, R⁹ is 5-chloro-4-methyl-imidazol-1-yl.

In another embodiment, R⁹ is:

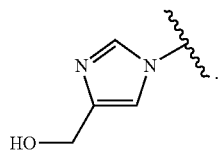

In another embodiment, R⁹ is:

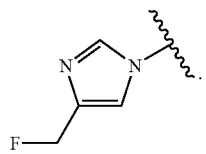 [SMILES: *n1cnc(CF)c1]

In another embodiment R¹⁰ is selected from the group consisting of aryl and aryl substituted with one or more R²¹ groups, and R⁹ is selected from the group consisting of heteroaryl and heteroaryl substituted with one or more R²¹ groups, and wherein each R²¹ is independently selected.

In another embodiment R¹⁰ is selected from the group consisting of phenyl and phenyl substituted with 1-3 independently selected R²¹ groups, and R⁹ is selected from the group consisting of imidazolyl and imidazolyl substituted with 1-3 independently selected R²¹ groups.

In another embodiment R¹⁰ is phenyl substituted with 1-3 independently selected R²¹ groups, and R⁹ is selected from the group consisting of imidazolyl and imidazolyl substituted with 1-3 independently selected R²¹ groups.

In another embodiment R¹⁰ is selected from the group consisting of heteroaryl and heteroaryl substituted with 1-3 R²¹ groups, and the R⁹ group is selected from the group consisting of heteroaryl and heteroaryl substituted with 1-3 R²¹ groups, and wherein each R²¹ is independently selected.

In another embodiment R¹⁰ is selected from the group consisting of pyridyl and pyridyl substituted with 1-3 R²¹ groups, and the R⁹ group is selected from the group consisting of imidazolyl and imidazolyl substituted with 1-3 R²¹ groups, and wherein each R²¹ is independently selected.

In another embodiment R¹⁰ is pyridyl, and the R⁹ group is imidazolyl substituted with 1-3 R²¹ groups, and wherein each R²¹ is independently selected.

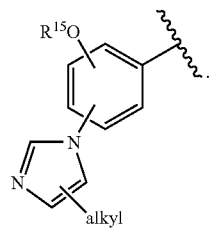

In another embodiment the R⁹-R¹⁰-moiety is:

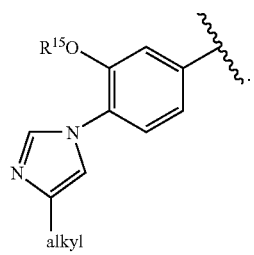

In another embodiment the R⁹-R¹⁰-moiety is:

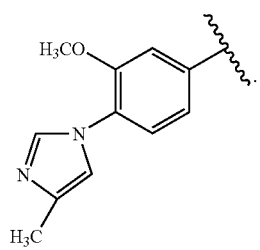 [SMILES: *c1ccc(-n2cnc(C)c2)c(OC)c1]

In another embodiment the R⁹-R¹⁰-moiety is:

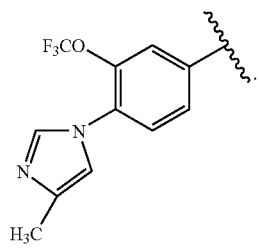 [SMILES: *c1ccc(-n2cnc(C)c2)c(OC(F)(F)F)c1]

In another embodiment the R$^9$-R$^{10}$-moiety is:

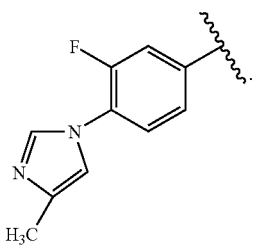 [SMILES: *c1ccc(-n2cnc(C)c2)c(F)c1]

In another embodiment R$^9$-R$^{10}$-moiety is:

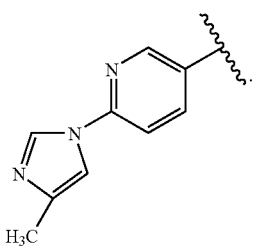 [SMILES: *c1ccc(-n2cnc(C)c2)nc1]

In another embodiment R$^9$-R$^{10}$-moiety is:

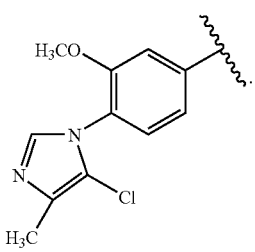 [SMILES: *c1ccc(-n2cnc(C)c2Cl)c(OC)c1]

In another embodiment, the present application discloses a compound, or pharmaceutically acceptable salts, solvates, esters or prodrugs of said compound, said compound having the general structure shown in Formula:

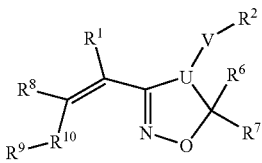

wherein the various moieties are defined above.

In another embodiment, this invention discloses a compound, or pharmaceutically acceptable salts, solvates, esters or prodrugs of said compound, said compound having the general structure shown in the formula:

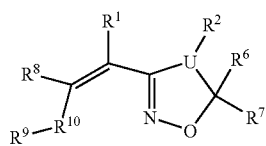

wherein U is C(R$^5$);
R$^1$ is H;
R$^2$ and R$^6$ are connected to form a 4-7 membered cycloalkyl ring;
R$^7$ is 3-(1,1'-biphenyl)-yl;
R$^8$ is H;
R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;
R$^{10}$ is phenyl; and
R$^9$ is imidazol-1-yl.

In another embodiment, this invention discloses a compound, or pharmaceutically acceptable salts, solvates, esters or prodrugs of said compound, said compound having the general structure shown in the formula:

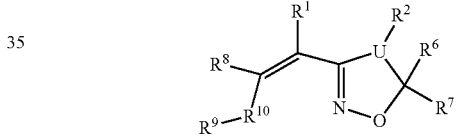

wherein U is C(R$^5$) or N;
R$^1$ is H;
R$^2$ and R$^6$ are connected to form a 5-7 membered heterocyclyl ring;
R$^7$ is phenyl;
R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;
R$^8$ is H;
R$^{10}$ is alkoxy-substituted phenyl; and
R$^9$ is 4-methyl-imidazol-1-yl.

In another embodiment, this invention discloses a compound, or pharmaceutically acceptable salts, solvates, esters or prodrugs of said compound, said compound having the general structure shown in the formula:

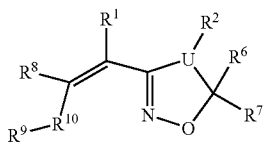

wherein U is C(R$^5$) or N;

R$^1$ is H;

R$^2$ and R$^6$ are connected to form a piperidinyl ring;

R$^7$ is 4-fluoro-phen-1-yl;

R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R$^8$ is H;

R$^{10}$ is phenyl; and

R$^9$ is imidazol-1-yl.

In another embodiment, this invention discloses a compound, or pharmaceutically acceptable salts, solvates, esters or prodrugs of said compound, said compound having the general structure shown in the formula:

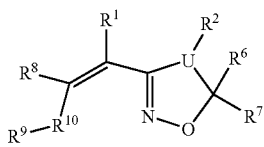

wherein U is C(R$^5$) or N;

R$^1$ is H;

R$^2$ and R$^6$ are connected to form a piperazinyl ring;

R$^7$ is 4-fluoro-phen-1-yl;

R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R$^8$ is H;

R$^{10}$ is phenyl; and

R$^9$ is 5-chloro-4-methyl-imidazol-1-yl.

In another embodiment, this invention discloses a compound, or pharmaceutically acceptable salts, solvates, esters or prodrugs of said compound, said compound having the general structure shown in the formula:

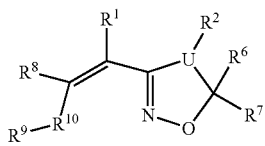

wherein U is C(R$^5$);

R$^1$ is H;

R$^2$ and R$^6$ are connected to form a cyclopentyl ring;

R$^7$ is 3-(1,1'-biphenyl)-yl;

R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R$^8$ is H;

R$^{10}$ is phenyl; and

R$^9$ is imidazol-1-yl.

In another embodiment, this invention discloses a compound, or pharmaceutically acceptable salts, solvates, esters or prodrugs of said compound, said compound having the general structure shown in the formula:

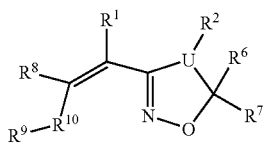

wherein U is C(R$^5$);

R$^1$ is H;

R$^7$ is alkyl;

R$^2$ and R$^6$ are connected to form a cyclopentyl ring;

R$^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

R$^8$ is H;

R$^{10}$ is phenyl; and

R$^9$ is imidazol-1-yl.

In another embodiment, this invention discloses a compound, or pharmaceutically acceptable salts, solvates, esters or prodrugs of said compound, said compound having the general structure shown in the formula:

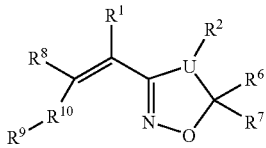

wherein U is C($R^5$) or N;

$R^1$ is H;

$R^2$ and $R^6$ are connected to form a piperidinyl ring;

$R^7$ is phenyl;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^8$ is H;

$R^{10}$ is phenyl; and $R^9$ is imidazol-1-yl.

In another embodiment, this invention discloses a compound, or pharmaceutically acceptable salts, solvates, esters or prodrugs of said compound, said compound having the general structure shown in the formula:

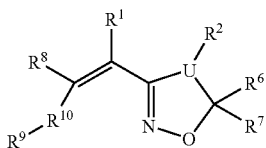

wherein U is C($R^5$) or N;

$R^1$ is H;

$R^7$ is H;

$R^2$ and $R^6$ are connected to form a piperazinyl ring;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^8$ is H;

$R^{10}$ is alkoxy-substituted phenyl; and $R^9$ is imidazol-1-yl.

In another embodiment, this invention discloses a compound, or pharmaceutically acceptable salts, solvates, esters or prodrugs of said compound, said compound having the general structure shown in the formula:

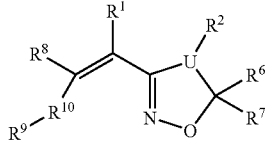

wherein U is C($R^5$) or N;

$R^1$ is H;

$R^7$ is (alkoxy)aryl-alkyl-;

$R^2$ and $R^6$ are connected to form a piperidinyl ring;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^8$ is H;

$R^{10}$ is (alkoxy-substituted)aryl; and $R^9$ is imidazol-1-yl.

In another embodiment, this invention discloses a compound, or pharmaceutically acceptable salts, solvates, esters or prodrugs of said compound, said compound having the general structure shown in the formula:

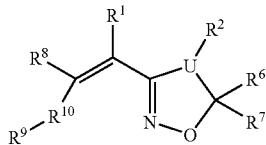

wherein U is C($R^5$) or N;

$R^1$ is H;

$R^2$ and $R^6$ are connected to form a piperazinyl ring;

$R^7$ is phenyl substituted with halo;

$R^5$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- can be unsubstituted or optionally independently substituted with 1-5 substituents which can be the same or different, each substituent being independently selected from the group consisting of moieties described earlier;

$R^8$ is H;

$R^{10}$ is (alkoxy-substituted)aryl; and $R^9$ is imidazol-1-yl.

In one embodiment the compound of formula I is selected from the group consisting of:
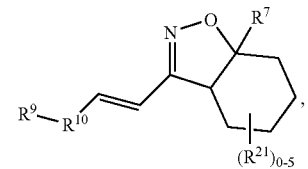
1A
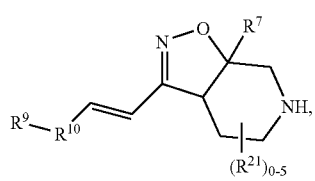
2A
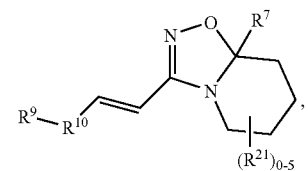
3A
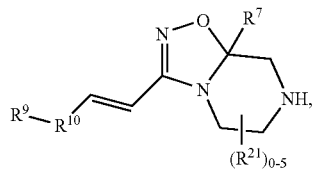
4A
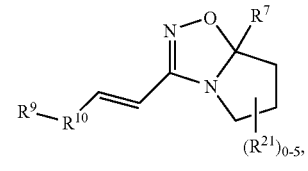
5A
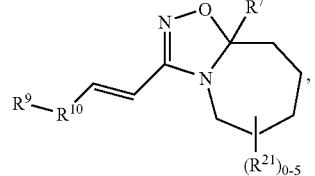
6A
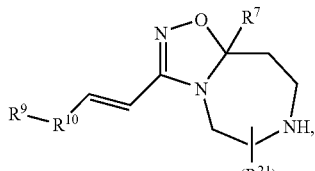
7A
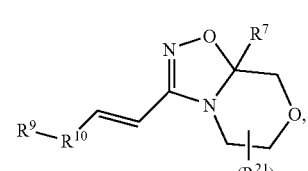
8A
-continued
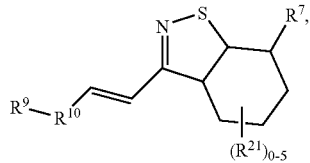
9A
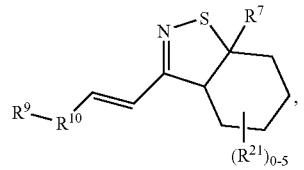
10A
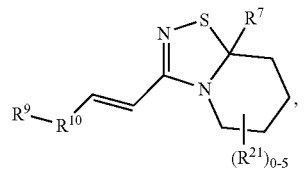
11A
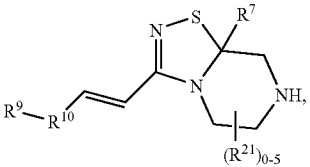
12A
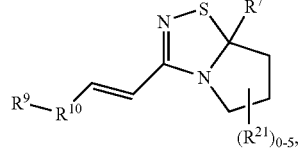
13A
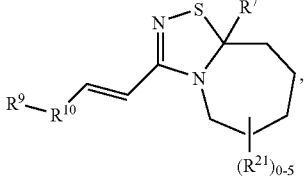
14A
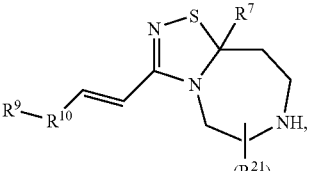
15A
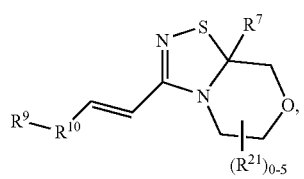
16A

| | |
|---|---|
| 17A 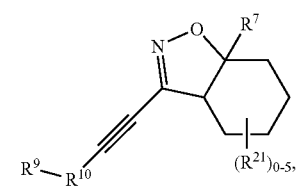 | 25A 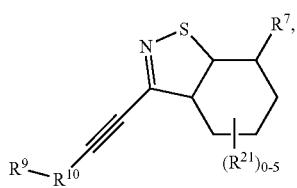 |
| 18A 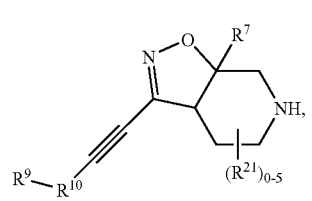 | 26A 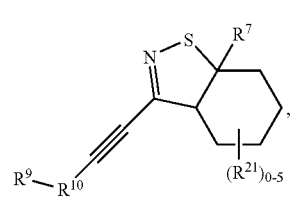 |
| 19A 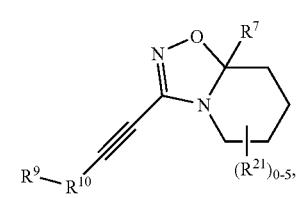 | 27A 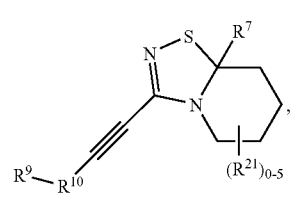 |
| 20A 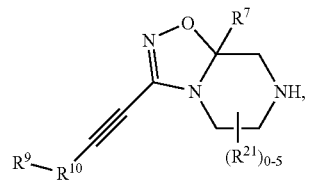 | 28A 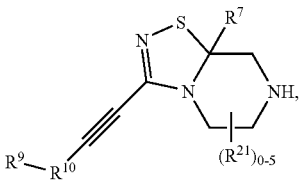 |
| 21A 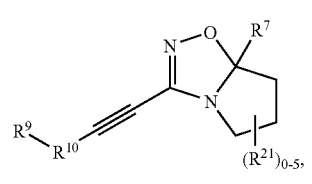 | 29A 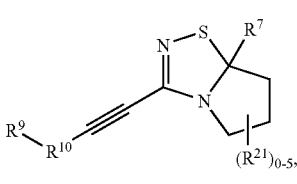 |
| 22A 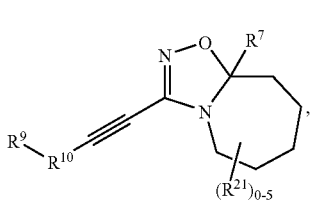 | 30A 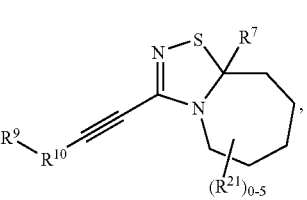 |
| 23A 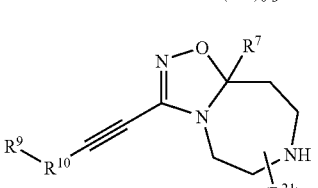 | 31A 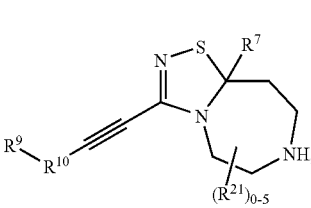 |
| 24A 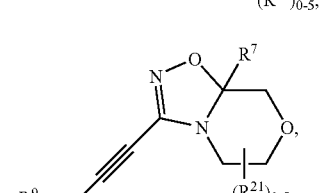 | 32A 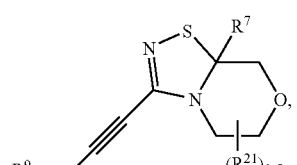 |

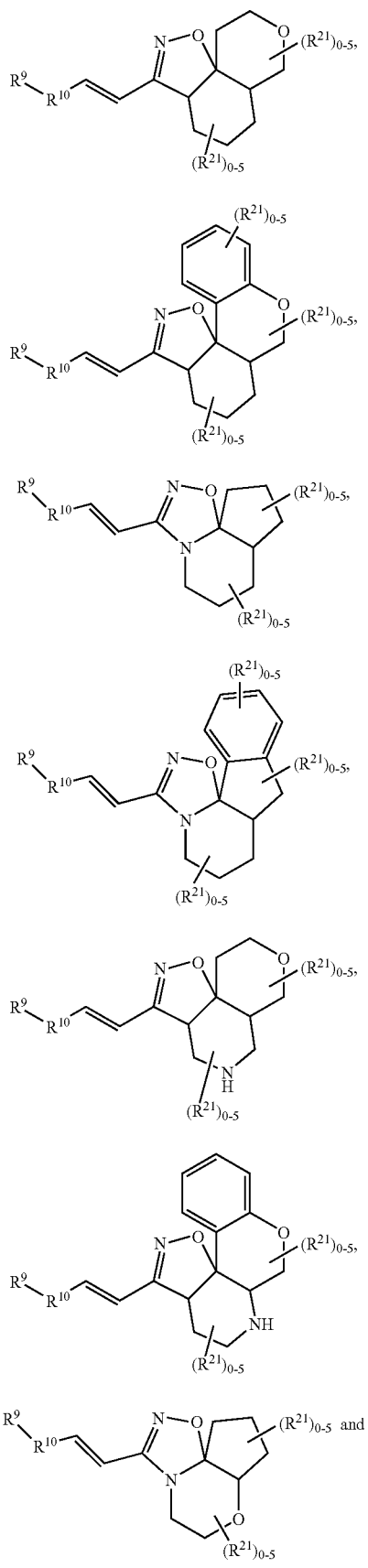

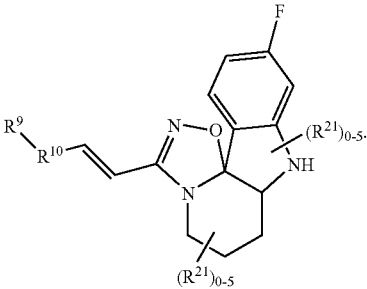

In another embodiment the compound of formula I is selected from the group consisting of: compounds 1A to 16A.

In another embodiment the compound of formula I is selected from the group consisting of: compounds 17A to 32A.

In another embodiment the compound of formula I is selected from the group consisting of: compounds 33A to 40A.

In another embodiment the compound of formula I is compound 1A.

In another embodiment the compound of formula I is compound 2A.

In another embodiment the compound of formula I is compound 3A.

In another embodiment the compound of formula I is compound 4A.

In another embodiment the compound of formula I is compound 5A.

In another embodiment the compound of formula I is compound 6A.

In another embodiment the compound of formula I is compound 7A.

In another embodiment the compound of formula I is compound 8A.

In another embodiment the compound of formula I is compound 9A.

In another embodiment the compound of formula I is compound 10A.

In another embodiment the compound of formula I is compound 11A.

In another embodiment the compound of formula I is compound 12A.

In another embodiment the compound of formula I is compound 13A.

In another embodiment the compound of formula I is compound 14A.

In another embodiment the compound of formula I is compound 15A.

In another embodiment the compound of formula I is compound 16A.

In another embodiment the compound of formula I is compound 17A.

In another embodiment the compound of formula I is compound 18A.

In another embodiment the compound of formula I is compound 19A.

In another embodiment the compound of formula I is compound 20A.

In another embodiment the compound of formula I is compound 21A.

In another embodiment the compound of formula I is compound 22A.

In another embodiment the compound of formula I is compound 23A.
In another embodiment the compound of formula I is compound 24A.
In another embodiment the compound of formula I is compound 25A.
In another embodiment the compound of formula I is compound 26A.
In another embodiment the compound of formula I is compound 27A.
In another embodiment the compound of formula I is compound 28A.
In another embodiment the compound of formula I is compound 29A.
In another embodiment the compound of formula I is compound 30A.
In another embodiment the compound of formula I is compound 31A.
In another embodiment the compound of formula I is compound 32A.
In another embodiment the compound of formula I is compound 33A.
In another embodiment the compound of formula I is compound 34A.
In another embodiment the compound of formula I is compound 35A.
In another embodiment the compound of formula I is compound 36A.
In another embodiment the compound of formula I is compound 37A.
In another embodiment the compound of formula I is compound 38A.
In another embodiment the compound of formula I is compound 39A.
In another embodiment the compound of formula I is compound 40A.

An illustrative group of compounds of the invention are shown in Table 1.

TABLE 1

| Structure | Obs. Mass | Retention Time (min) |
|---|---|---|
| 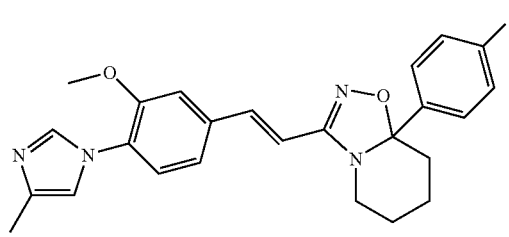 1 | 433.2 | 3.02 |
| 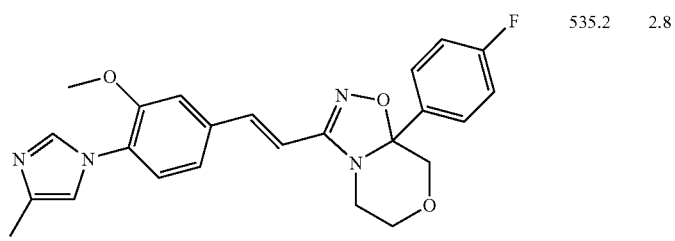 2 | 535.2 | 2.8 |
| 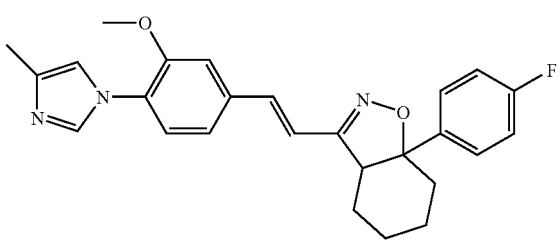 3 | — | — |

TABLE 1-continued
| Structure | Obs. Mass | Retention Time (min) |
|---|---|---|
| 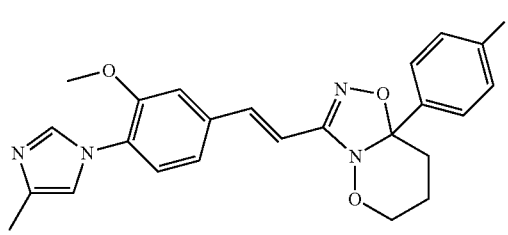 4 | — | — |
| 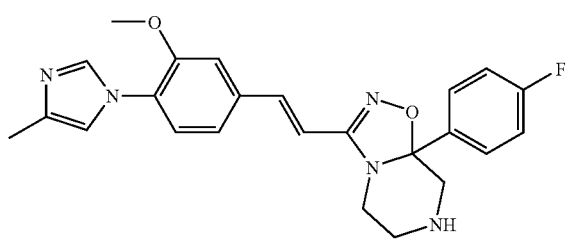 5 | — | — |
| 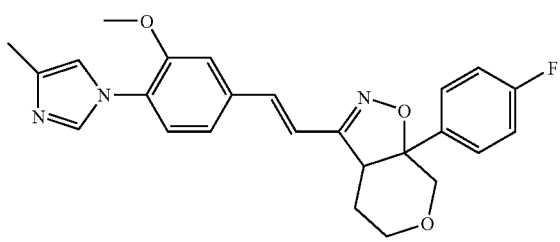 6 | — | — |
| 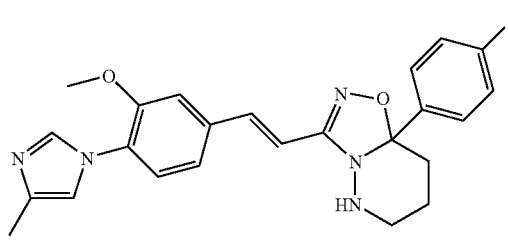 7 | — | — |
| 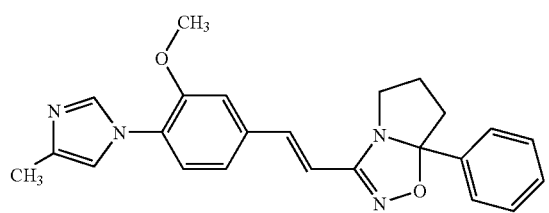 9 | 401.2 | 2.9 |

TABLE 1-continued

| Structure | Obs. Mass | Retention Time (min) |
|---|---|---|
| 10 | 401.2 | 3.04 |
| 11 | 435.2 | 3.21 |
| 12 | 435.2 | 3.26 |
| 13 | 435.2 | 3.25 |

TABLE 1-continued
| Structure | Obs. Mass | Retention Time (min) |
|---|---|---|
| 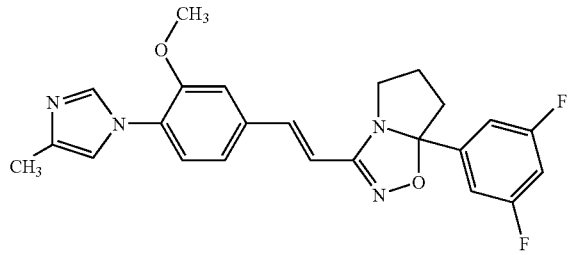 14 | 451.2 | 4.82 |
| 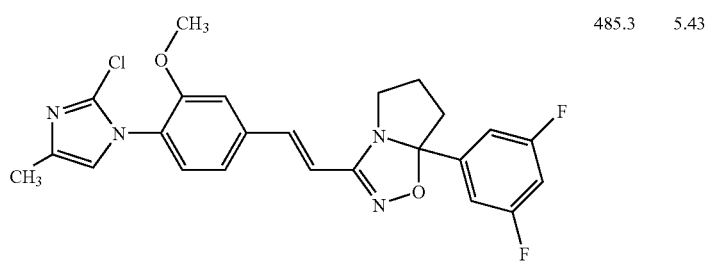 15 | 485.3 | 5.43 |
| 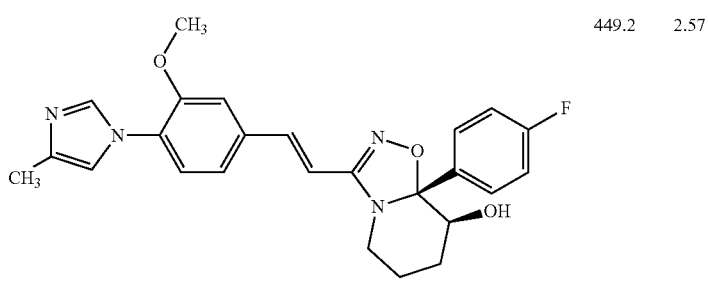 16 | 449.2 | 2.57 |
| 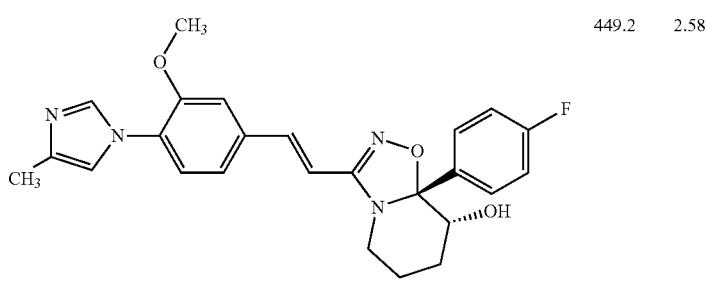 17 | 449.2 | 2.58 |

TABLE 1-continued

| Structure | Obs. Mass | Retention Time (min) |
|---|---|---|
| 18 | 445.2 | 3.06 |
| 19 | 461.2 | 2.87 |
| 20 | 463.3 | 3.22 |
| 21 | 461.3 | 2.99 |

TABLE 1-continued

| Structure | Obs. Mass | Retention Time (min) |
|---|---|---|
| 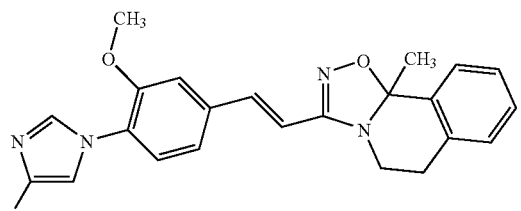 22 | 401.2 | 3.08 |

In one embodiment the compound of formula I is compound 1.

In another embodiment the compound of formula I is compound 2.

In another embodiment the compound of formula I is compound 3.

In another embodiment the compound of formula I is compound 4.

In another embodiment the compound of formula I is compound 5.

In another embodiment the compound of formula I is compound 6.

In another embodiment the compound of formula I is compound 7.

In another embodiment the compound of formula I is compound 9.

In another embodiment the compound of formula I is compound 10.

In another embodiment the compound of formula I is compound 11.

In another embodiment the compound of formula I is compound 12.

In another embodiment the compound of formula I is compound 13.

In another embodiment the compound of formula I is compound 14.

In another embodiment the compound of formula I is compound 15.

In another embodiment the compound of formula I is compound 16.

In another embodiment the compound of formula I is compound 17.

In another embodiment the compound of formula I is compound 18.

In another embodiment the compound of formula I is compound 19.

In another embodiment the compound of formula I is compound 20.

In another embodiment the compound of formula I is compound 21.

In another embodiment the compound of formula I is compound 22.

As used above, and throughout this disclosure, the following terms, unless otherwise indicated, shall be understood to have the following meanings:

"At least one" means one or more than one, for example, 1, 2 or 3, or in another example 1 or 2, or in another example 1.

"One or more" with reference to the use of the compounds of this invention means that one or more than one compound is used, for example, 1, 2 or 3, or in another example, 1 or 2, or in another example 1.

"Patient" includes both human and animals.

"Mammal" means humans and other mammalian animals.

It is noted that the carbons of formula I and other formulas herein may be replaced with 1 to 3 silicon atoms so long as all valency requirements are satisfied.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

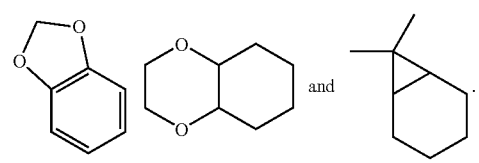

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a heterocyclyl ring wherein a single moiety (e.g., =O) simultaneously replaces two available hydrogens on the same carbon atom on a ring system. An example of such moiety is pyrrolidone:

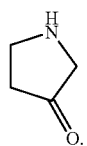

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

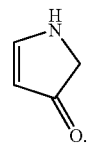

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

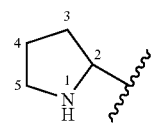

there is no —OH attached directly to carbons marked 2 and 5.

It should also be noted that tautomeric forms such as, for example, the moieties:

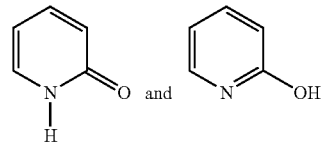 [SMILES: O=c1cccc[nH]1 ; "and" ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent, moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl. "Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidine-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide, enol, keto or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{18}F$, and $^{35}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention can have pharmacological properties; in particular, the compounds of Formula I can be modulators of gamma secretase (including inhibitors, antagonists and the like).

More specifically, the compounds of Formula I can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula I, or a pharmaceutically acceptable salt, solvate, ester or prodrug of said compound to the mammal.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula I, or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula I, or a pharmaceutically acceptable salt, solvate, ester or prodrug of said compound and at least one pharmaceutically acceptable carrier.

Other embodiments of this invention are directed to pharmaceutically acceptable salts of any one of the embodiments above directed to any one of compounds 1 to 7 and 9 to 22.

Other embodiments of this invention are directed to pharmaceutically acceptable esters of any one of the embodiments above directed to any one of compounds 1 to 7 and 9 to 22.

Other embodiments of this invention are directed to solvates of any one of the embodiments above directed to any one of compounds 1 to 7 and 9 to 22.

One embodiment of this invention is directed to a compound of formula I.

Another embodiment of this invention is directed to a pharmaceutically acceptable salt of a compound of formula I.

Another embodiment of this invention is directed to a pharmaceutically acceptable ester of a compound of formula I.

Another embodiment of this invention is directed to a solvate of a compound of formula I.

Another embodiment of this invention is directed to a compound of formula I in isolated form.

Another embodiment of this invention is directed to a compound of formula I in pure form.

Another embodiment of this invention is directed to a compound of formula I in pure and isolated form.

Another embodiment of this invention is directed to a pharmaceutical composition comprising an effective amount of one or more (e.g., one) compounds of formula I and a pharmaceutically acceptable carrier.

Another embodiment of this invention is directed to a pharmaceutical composition comprising an effective amount of a pharmaceutically acceptable salt of one or more (e.g., one) compounds of formula I and a pharmaceutically acceptable carrier.

Another embodiment of this invention is directed to a pharmaceutical composition comprising an effective amount of a pharmaceutically acceptable ester of one or more (e.g., one) compounds of formula I and a pharmaceutically acceptable carrier.

Another embodiment of this invention is directed to a pharmaceutical composition comprising an effective amount of a solvate of one or more (e.g., one) compounds of formula I and a pharmaceutically acceptable carrier.

Another embodiment of this invention is directed to a pharmaceutical composition comprising an effective amount of one or more (e.g., one) compounds of formula I, and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of formula I, and effective amount of one or more BACE inhibitors, and a pharmaceutically acceptable carrier.

Another embodiment of this invention is directed to a pharmaceutical composition comprising an effective amount of one or more (e.g., one) compounds of formula I, and effective amount of one or more cholinesterase inhibitors (e.g., acetyl- and/or butyrylchlolinesterase inhibitors), and a pharmaceutically acceptable carrier.

The compounds of formula I can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective amount of one or more (e.g., one) compounds of formula I to a patient in need of such treatment.

Another embodiment of this invention is directed to a method for modulating (including inhibiting, antagonizing and the like) gamma-secretase, comprising administering an effective amount of a compound of formula I to a patient in need of treatment.

Another embodiment of this invention is directed to a method of treating one or more neurodegenerative diseases, comprising administering an effective amount of one or more (e.g., one) compounds of formula I to a patient in need of treatment.

Another embodiment of this invention is directed to a method of treating one or more neurodegenerative diseases, comprising administering an effective amount of a compound of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of formula I to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of formula I to a patient in need of treatment.

Another embodiment of this invention is directed to a method of treating Alzheimer's disease, comprising administering an effective amount of one or more (e.g., one) compounds of formula I to a patient in need of treatment.

Another embodiment of this invention is directed to a method of treating Alzheimer's disease, comprising administering an effective amount of a compound of formula I to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula I and the administration of an effective amount of one or more (e.g., one) other pharmaceutical active ingredients (e.g., drugs). The compounds of formula I and the other drugs can be administered separately (i.e., each is in its own separate dosage form), or the compounds of formula I can be combined with the other drugs in the same dosage form.

Thus, other embodiments of this invention are directed to any one of the methods of treatment, or methods of inhibiting, described herein, wherein an effective amount of the compound of formula I is used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective amount of one or more (e.g., one) compounds of formula I, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of formula I, in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of formula I, in combination with an effective amount of one or more BACE inhibitors.

Another embodiment of this invention is directed to a method of treating Alzheimer's disease, comprising administering an effective amount of one or more compounds of formula I, in combination with an effective amount of Exelon (rivastigmine).

Another embodiment of this invention is directed to a method of treating Alzheimer's disease, comprising administering an effective amount of one or more compounds of formula I, in combination with an effective amount of Cognex (tacrine).

Another embodiment of this invention is directed to a method of treating Alzheimer's disease, comprising administering an effective amount of one or more compounds of formula I, in combination with an effective amount of a Tau kinase inhibitor.

Another embodiment of this invention is directed to a method of treating Alzheimer's disease, comprising administering an effective amount of one or more compounds of formula I, in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula I, in combination with an effective amount of one anti-Abeta vaccination (active immunization).

Another embodiment of this invention is directed to a method of treating Alzheimer's disease, comprising administering an effective amount of one or more compounds of formula I, in combination with an effective amount of one or more APP ligands.

Another embodiment of this invention is directed to a method of treating Alzheimer's disease, comprising administering an effective amount of one or more compounds of formula I, in combination with an effective amount of one or more agents that upregulate insulin degrading enzyme and/or neprilysin.

Another embodiment of this invention is directed to a method of treating Alzheimer's disease, comprising administering an effective amount of one or more compounds of formula I, in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula I, in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula I, in combination with an effective amount of one or more LXR agonists.

Another embodiment of this invention is directed to a method of treating Alzheimer's disease, comprising administering an effective amount of one or more compounds of formula I, in combination with an effective amount of one or more LRP mimics.

Another embodiment of this invention is directed to a method of treating Alzheimer's disease, comprising administering an effective amount of one or more compounds of formula I, in combination with an effective amount of one or more 5-HT6 receptor antagonists.

Another embodiment of this invention is directed to a method of treating Alzheimer's disease, comprising administering an effective amount of one or more compounds of formula I, in combination with an effective amount of one or more nicotinic receptor agonists.

Another embodiment of this invention is directed to a method of treating Alzheimer's disease, comprising administering an effective amount of one or more compounds of formula I, in combination with an effective amount of one or more H3 receptor antagonists.

This invention also provides a method of treating Alzheimer's disease, comprising administering an effective amount of one or more compounds of formula I, in combination with an effective amount of one or more histone deacetylase inhibitors.

Another embodiment of this invention is directed to a method of treating Alzheimer's disease, comprising administering an effective amount of one or more compounds of formula I, in combination with an effective amount of one or more hsp90 inhibitors.

Another embodiment of this invention is directed to a method of treating Alzheimer's disease, comprising administering an effective amount of one or more compounds of formula I, in combination with an effective amount of one or more m1 muscarinic receptor agonists.

Another embodiment of this invention is directed to a method of treating Alzheimer's disease, comprising administering an effective amount of one or more compounds of formula I, in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds of formula I, in combination with an effective amount of one or more mGluR2/3 antagonists.

Another embodiment of this invention is directed to a method of treating Alzheimer's disease, comprising administering an effective amount of one or more compounds of formula I, in combination with an effective amount of one or more anti-inflammatory agents that can reduce neuroinflammation.

Another embodiment of this invention is directed to a method of treating Alzheimer's disease, comprising administering an effective amount of one or more compounds of formula I, in combination with an effective amount of one or more Prostaglandin EP2 receptor antagonists.

This invention also provides a method of treating Alzheimer's disease, comprising administering an effective amount of one or more compounds of formula I, in combination with an effective amount of one or more PAI-1 inhibitors:

This invention also provides a method of treating Alzheimer's disease, comprising administering an effective amount of one or more compounds of formula I, in combination with an effective amount of one or more agents that can induce Abeta efflux such as gelsolin.

This invention also provides a method of treating Downs syndrome, comprising administering an effective amount of one or more (e.g., one) compounds of formula I to a patient in need of treatment.

This invention also provides a method of treating Downs syndrome, comprising administering an effective amount of a compound of formula I to a patient in need of treatment.

This invention also provides a method of treating Downs syndrome, comprising administering an effective amount of one or more (e.g., one) compounds of formula I, in combination with an effective amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective amount of a compound of formula I, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating mild cognitive impairment, comprising administering an effective amount of one or more (e.g., one) compounds of formula I to a patient in need of treatment.

This invention also provides a method of treating glaucoma, comprising administering an effective amount of one or more (e.g., one) compounds of formula I to a patient in need of treatment.

This invention also provides a method of treating cerebral amyloid angiopathy, comprising administering an effective amount of one or more (e.g., one) compounds of formula I to a patient in need of treatment.

This invention also provides a method of treating stroke, comprising administering an effective amount of one or more (e.g., one) compounds of formula I to a patient in need of treatment.

This invention also provides a method of treating dementia, comprising administering an effective amount of one or more (e.g., one) compounds of formula I to a patient in need of treatment.

This invention also provides a method of treating microgliosis, comprising administering an effective amount of one or more (e.g., one) compounds of formula I to a patient in need of treatment.

This invention also provides a method of treating brain inflammation, comprising administering an effective amount of one or more (e.g., one) compounds of formula I to a patient in need of treatment.

This invention also provides a method of treating olfactory function loss, comprising administering an effective amount of one or more (e.g., one) compounds of formula I to a patient in need of treatment.

This invention also provides combinations (i.e., pharmaceutical compositions) comprising an effective amount of one or more (e.g., one) compounds of formula I, in combination with an effective amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula I in a pharmaceutically acceptable carrier, and another container (i.e., a second container) comprises an effective amount of another pharmaceutically active ingredient (as described above), the combined quantities of the compound of formula I and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a pharmaceutically acceptable salt of a compound of formula (I), said compound of formula (I) being selected from the group consisting of: 1A to 40A.

Another embodiment of this invention is directed to a pharmaceutically acceptable ester of a compound of formula (I), said compound of formula (I) being selected from the group consisting of: 1A to 40A.

Another embodiment of this invention is directed to a solvate of a compound of formula (I), said compound of formula (I) being selected from the group consisting of: 1A to 40A.

Another embodiment of this invention is directed to a compound of formula (I) in isolated form, said compound of formula (I) being selected from the group consisting of: 1A to 40A.

Another embodiment of this invention is directed to a compound of formula (I) in pure form, said compound of formula (I) being selected from the group consisting of: said compound of formula (I) being selected from the group consisting of: 1A to 40A.

Another embodiment of this invention is directed to a compound of formula (I) in pure and isolated form, said compound of formula (I) being selected from the group consisting of: said compound of formula (I) being selected from the group consisting of: 1A to 40A.

Another embodiment is directed to a pharmaceutical composition comprising an effective amount of one or more (e.g., one) compounds of formula (I) and a pharmaceutically acceptable carrier, said compound of formula (I) being selected from the group consisting of: said compound of formula (I) being selected from the group consisting of: 1A to 40A.

Another embodiment is directed to a pharmaceutical composition comprising an effective amount of a pharmaceutically acceptable salt of one or more (e.g., one) compounds of formula (I) and a pharmaceutically acceptable carrier, said compound of formula (I) being selected from the group consisting of: said compound of formula (I) being selected from the group consisting of: 1A to 40A.

Another embodiment is directed to a pharmaceutical composition comprising an effective amount of a pharmaceutically acceptable ester of one or more (e.g., one) compounds of formula (I) and a pharmaceutically acceptable carrier, said compound of formula (I) being selected from the group consisting of: said compound of formula (I) being selected from the group consisting of: 1A to 40A.

Another embodiment is directed to a pharmaceutical composition comprising an effective amount of a solvate of one or more (e.g., one) compounds of formula (I) and a pharmaceutically acceptable carrier, said compound of formula (I) being selected from the group consisting of: said compound of formula (I) being selected from the group consisting of: 1A to 40A.

Another embodiment of this invention is directed to a pharmaceutical composition comprising an effective amount of one or more (e.g., one) compounds of formula (I), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase, said compound of formula (I) being selected from the group consisting of: said compound of formula (I) being selected from the group consisting of: 1A to 40A.

Another embodiment of this invention is directed to a pharmaceutical composition comprising an effective amount of one or more (e.g., one) compounds of formula (I), and effective amount of one or more BACE inhibitors, and a pharmaceutically acceptable carrier, said compound of formula (I) being selected from the group consisting of: said compound of formula (I) being selected from the group consisting of: 1A to 40A.

Another embodiment of this invention is directed to a pharmaceutical composition comprising an effective amount of one or more (e.g., one) compounds selected from the group consisting of: 1A to 40A, and an effective amount of one or more cholinesterase inhibitors (e.g., acetyl- and/or butyryl-chlolinesterase inhibitors), and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more muscarinic antagonists (e.g., $m_1$ agonists or $m_2$ antagonists), and a pharmaceutically acceptable carrier.

Another embodiment of this invention is directed to a pharmaceutical composition comprising an effective amount of one or more (e.g., one) compounds selected from the group consisting of: 1A to 40A, and effective amount of Exelon (rivastigmine), and a pharmaceutically acceptable carrier.

Another embodiment of this invention is directed to a pharmaceutical composition comprising an effective amount of one or more (e.g., one) compounds selected from the group consisting of: 1A to 40A, and effective amount of Cognex (tacrine), and a pharmaceutically acceptable carrier.

Another embodiment of this invention is directed to a pharmaceutical composition comprising an effective amount of one or more (e.g., one) compounds selected from the group consisting of: 1A to 40A, and effective amount of a Tau kinase inhibitor, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds selected from the group consisting of: 1A to 40A, and effective amount of one anti-Abeta vaccine (active immunization), and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more APP ligands, and a pharmaceutically acceptable carrier.

Another embodiment of this invention is directed to a pharmaceutical composition comprising an effective amount of one or more (e.g., one) compounds selected from the group consisting of: consisting of: 1A to 40A, and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more cholesterol lowering agents (for example, statins such as Atorvastatin, Fluvastatin, Lovastatin, Mevastatin, Pitavastatin, Pravastatine, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds selected from the group consisting of: consisting of: 1A to 40A, and effective amount of one or more fibrates (for example, clofibrate, Clofibride, Etofibrate, Aluminium Clofibrate), and a pharmaceutically acceptable carrier.

Another embodiment of this invention is directed to a pharmaceutical composition comprising an effective amount of one or more (e.g., one) compounds selected from the group consisting of: consisting of: 1A to 40A, and effective amount of one or more LXR agonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more LRP mimics, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more 5-HT6 receptor antagonists, and a pharmaceutically acceptable carrier.

Another embodiment of this invention is directed to a pharmaceutical composition comprising an effective amount of one or more (e.g., one) compounds selected from the group consisting of: consisting of: 1A to 40A, and effective amount of one or more nicotinic receptor agonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more H3 receptor antagonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more histone deacetylase inhibitors, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more hsp90 inhibitors, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more m1 muscarinic receptor agonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more one mGluR2/3 antagonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more PAI-1 inhibitors, and a pharmaceutically acceptable carrier.

Another embodiment of this invention is directed to a pharmaceutical composition comprising an effective amount of one or more (e.g., one) compounds selected from the group consisting of: 1A to 40A, and effective amount of one or more agents that can induce Abeta efflux such as gelsolin, and a pharmaceutically acceptable carrier.

The compounds of formulas (I) selected from the group consisting of: 1A to 40A can be useful as gamma secretase modulators and can be useful in the treatment and prevention of diseases such as, for example, central nervous system disorders (such as Alzheimers disease and Downs Syndrome), and treating mild cognitive impairment, glaucoma, cerebral amyloid angiopathy, stroke, dementia, microgliosis, brain inflammation, and olfactory function loss.

Thus, another embodiment of this invention is directed to a method for modulating (including inhibiting, antagonizing and the like) gamma-secretase comprising administering an effective (i.e., therapeutically effective) amount of one or more (e.g., one) compounds of formula (I) to a patient in need of such treatment, said compound of formula (I) being selected from the group consisting of: 1A to 40A.

Another embodiment of this invention is directed to a method for modulating (including inhibiting, antagonizing and the like) gamma-secretase, comprising administering an effective (i.e., therapeutically effective) amount of a compound of formula (I) to a patient in need of treatment, said compound of formula (I) being selected from the group consisting of: 1A to 40A.

Another embodiment of this invention is directed to a method of treating one or more neurodegenerative diseases, comprising administering an effective (i.e., therapeutically effective) amount of one or more (e.g., one) compounds of formula (I) to a patient in need of treatment, said compound of formula (I) being selected from the group consisting of: 1A to 40A.

Another embodiment of this invention is directed to a method of treating one or more neurodegenerative diseases, comprising administering an effective (i.e., therapeutically effective) amount of a compound of formula (I) to a patient in need of treatment, said compound of formula (I) being selected from the group consisting of: 1A to 40A.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of formula (I) to a patient in need of treatment, said compound of formula (I) being selected from the group consisting of: 1A to 40A.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of formula (I) to a patient in need of treatment, said compound of formula (I) being selected from the group consisting of: 1A to 40A.

Another embodiment of this invention is directed to a method of treating Alzheimer's disease, comprising administering an effective (i.e., therapeutically effective) amount of one or more (e.g., one) compounds of formula (I) to a patient in need of treatment, said compound of formula (I) being selected from the group consisting of: 1A to 40A.

Another embodiment of this invention is directed to a method of treating Alzheimer's disease, comprising administering an effective (i.e., therapeutically effective) amount of a compound of formula (I) to a patient in need of treatment, said compound of formula (I) being selected from the group consisting of: 1A to 40A.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula (I) to a patient in need of treatment, said compound of formula (I) being selected from the group consisting of: 1A to 40A.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula (I) to a patient in need of treatment, said compound of formula (I) being selected from the group consisting of: 1A to 40A.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I), and the administration of one or more (e.g., one) other pharmaceutical active ingredients (e.g., drugs). The compounds of formula (I), and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein the compounds of formula (I) are used in combination with an effective amount of one or more other pharmaceutically active ingredients selected from the group consisting of: BACE inhibitors (beta secretase inhibitors); muscarinic antagonists (e.g., $m_1$ agonists or $m_2$ antagonists); cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) selected from the group consisting of: 1A to 40A, and the administration of one or more (e.g., one) other pharmaceutical active ingredients (e.g., drugs). The compounds of formula 1A to 40A, and the other drugs can be administered separately (i.e., each is in its own separate dosage form), or the compounds of formula 1A to 40A can be combined with the other drugs in the same dosage form.

Thus, other embodiments of this invention are directed to any one of the methods of treatment, or methods of inhibiting, described herein, wherein the compounds of formula (I), selected from the group consisting of: 1A to 40A are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Other embodiments of this invention are directed to any one of the methods of treatment, or methods of inhibiting, described herein, wherein the compounds of formula (I), selected from the group consisting of: 1A to 40A are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; and cholesterol absorption inhibitors (e.g., ezetimibe).

Other embodiments of this invention are directed to any one of the methods of treatment, or methods of inhibiting, described herein, wherein the compounds of formula (I), selected from the group consisting of: 1A to 40A are used in combination with an effective amount of one or more other pharmaceutically active ingredients selected from the group consisting of: Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective (i.e., therapeutically effective) amount of one or more (e.g., one) compounds of formula (I) selected from the group consisting of: 1A to 40A, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of formula (I) selected from the group consisting of: 1A to 40A, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of formula (I) selected from the group consisting of: in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of formula (I) selected from the group consisting of: 1A to 40A, in combination with an effective (i.e., therapeutically effective) amount of one or more BACE inhibitors.

Another embodiment of this invention is directed to a method of treating Alzheimer's disease, comprising administering an effective (i.e., therapeutically effective) amount of a compound of formula (I) selected from the group consisting of: 1A to 40A, and the Compound of Example 1, in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds of formula (I) selected from the group consisting of: 1A to 40A to a patient in need of treatment.

Another embodiment of this invention is directed to a method of treating Downs syndrome, comprising administering an effective (i.e., therapeutically effective) amount of a compound of formula (I) selected from the group consisting of: 1A to 40A, to a patient in need of treatment.

Another embodiment of this invention is directed to a method of treating Downs syndrome, comprising administering an effective (i.e., therapeutically effective) amount of one or more (e.g., one) compounds of formula (I) selected from the group consisting of: 1A to 40A, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of formula (I) selected from the group consisting of: 1A to 40A, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of formula (I) selected from the group consisting of: 1A to 40A in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of one or more (e.g., one) compounds of formula (I) (e.g., compounds selected from the group consisting of: 1A to 40A in a pharmaceutically acceptable carrier, and another container (i.e., a second container) comprises an effective amount of another pharmaceutically active ingredient (as described above), the combined quantities of the compounds of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound selected from the group consisting of the compounds of formulas (I) (e.g. the compounds selected from the group consisting of: 1A to 40A) in a pharmaceutically acceptable carrier, and another container (i.e., a second container) comprises an effective amount of another pharmaceutically active ingredient (as described above), the combined quantities of the compound of formulas (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above methods of treatment, pharmaceutical compositions, or kits wherein the compound of formula I is any one of the compounds 1 to 7 and 9 to 22

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 2007 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. application Ser. No. 60/874,362 filed Dec. 12, 2006, and U.S. Application Ser. No. 60/874,419 filed Dec. 12, 2006, the disclosures of each being incorporated herein by reference thereto.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt, solvate, ester or prodrug of said compound and a pharmaceutically acceptable carrier, vehicle or diluent.

Yet another aspect of this invention is a kit comprising an amount of at least one compound of Formula I, or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following example which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion is given.

EXAMPLES

Method A, Compound 1 of Table 1

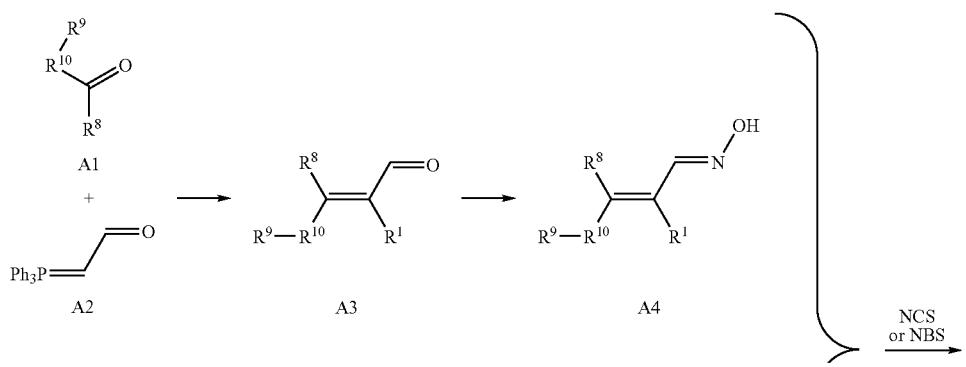

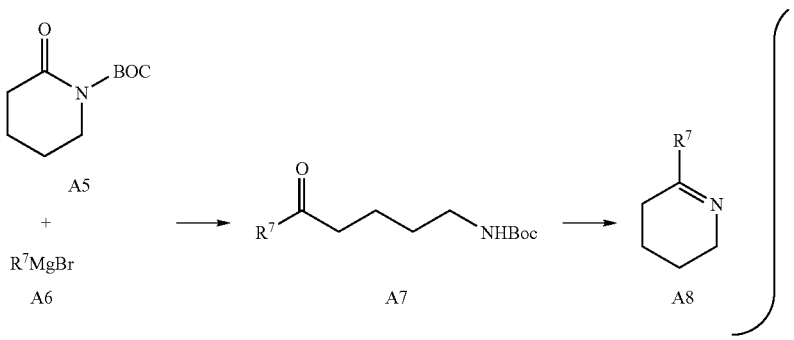

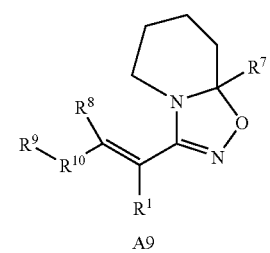

Method A, Step 1

The following method was adapted for the oxadiazoline synthesis (Tsuge, Otohiko; Kanemasa, Shuji; Suga, Hiroyuki; Nakagawa, Norihiko. *Bulletin of the Chemical Society of Japan* (1987), 60(7), 2463-73).

Compound A1 ($R^8$=H, $R^{19}$=3-MeO-Phenyl, $R^9$=4-(4-Methylimidazol-1-yl), 3 g) and A2 (4.2 g) in 135 ml of anhydrous THF was heated at 100° C. in a sealed tube under nitrogen overnight. Solvent was evaporated and residue chromatographed using a silica gel column eluted with EtOAc/Hexane to give 2.7 g of A3 ($R^1$=H, $R^8$=H, $R^{10}$=3-OMePhenyl, $R^9$=4-(4-Methyl-imidazol-1-yl)).

Method A, Step 2

A3 ($R^1$=H, $R^8$=H, $R^{10}$=3-MeO-Phenyl, $R^9$=4-(4-Methyl-imidazol-1-yl), 2.7 g) and potassium acetate (1.4 g) in 120 mL MeOH was cooled to 0° C. before hydoxylamine hydrochloride (1 g) was added. The reaction mixture was stirred for 90 min before the solvent was evaporated. The residue was partitioned in EtOAc and brine. The organic layer was dried over anhydrous $Na_2SO_4$. The crude was purified on C18 reverse phase column to give 1 g of A4 ($R^1$=H, $R^8$=H, $R^{10}$=3-MeO-Phenyl, $R^9$=4-(4-Methyl-imidazol-1-yl)).

MS (M+1): 258.

Method A, Step 3

To the solution of A5 (1.98 g, 9.94 mmol) in 30 ml of anhydrous THF at −78° C. was slowly added A6 ($R^7$=4-Fluorophenyl, 11.9 ml, 11.92 mmol) over 20 minutes. The mixture was warmed up to r.t. and stirred at r.t. overnight. The reaction was quenched by adding 2M HCl aqueous solution to PH=3, the mixture was extracted with $CH_2Cl_2$, washed with brine, dried over $Na_2SO_4$, filtered. The filtrate was concentrated and purified by Isco using 20% of EtOAc/Hexane. Yield: 1.4 g of A7. $^1$H NMR ($CDCl_3$ 400 MHz): 7.96 (m, 2H), 7.10 (t, J=8.8 Hz, 2H), 4.64 (bs, 1H), 3.15 (m, 2H), 2.95 (t, J=7.3 Hz, 2H), 1.75 (m, 2H), 1.55 (m, 2H), 1.42 (s, 9H).

Method A, Step 4

To the solution of A7 ($R^7$=4-Fluorophenyl, 0.9 g, 3.05 mmol) in 3 ml of TFA was added 3A molecular sieves. After stirring at room temperature for 4 h, the reaction was neutralized by adding saturated $NaHCO_3$ aqueous solution to PH=10, the mixture was extracted with $CH_2Cl_2$, washed with brine, dried over $Na_2SO_4$, and filtered. The residue is pure A8. Yield: 0.46 g. MH$^+$: 178.2.

Method A, Step 5

To the solution of A4 (0.098 g, 0.381 mmol) in 2 ml of DCM was added NCS (0.051 g, 0.381 mmol) at 0° C. After stirring at 0° C. for 1 h, A8 (0.068 g, 0.381 mmol) and $Et_3N$ (0.08 ml, 0.572 mmol) in 1 ml of DCM was added at 0° C. the mixture was then stirred at r.t. for 24 h, extracted with $CH_2Cl_2$ and brine, dried over $Na_2SO_4$, filtered, concentrated and purified by reverse-phase HPLC to give 0.035 g of A9 ($R^1$=$R^8$=H, $R^{10}$=3-OMePhenyl, $R^9$=4-(4-Methyl-imidazol-1-yl, $R^7$=4-Fluorophenyl). $^1$H NMR ($CDCl_3$ 400 MHz): 7.74 (s, 1H), 7.64 (m, 2H), 7.4 (d, J=16.4 Hz, 1H), 7.26 (m, 1H), 7.17 (dd, J=8.2 and 1.6 Hz, 1H), 7.07-7.13 (m, 3H), 6.94 (s, 1H), 6.52 (d, J=16.4 Hz, 1H), 3.90 (s, 3H), 3.65 (m, 1H), 3.08 (m, 1H), 2.19-2.40 (m, 5H), 1.90 (m, 1H), 1.60 (m, 2H), 1.48 (m, 1H). MS (M+1): 433.2.

The compounds 1-7 and 9-15 in Table 1 were synthesized using methods similar to that of Method A.

Method B, Compound 18 of Table 1

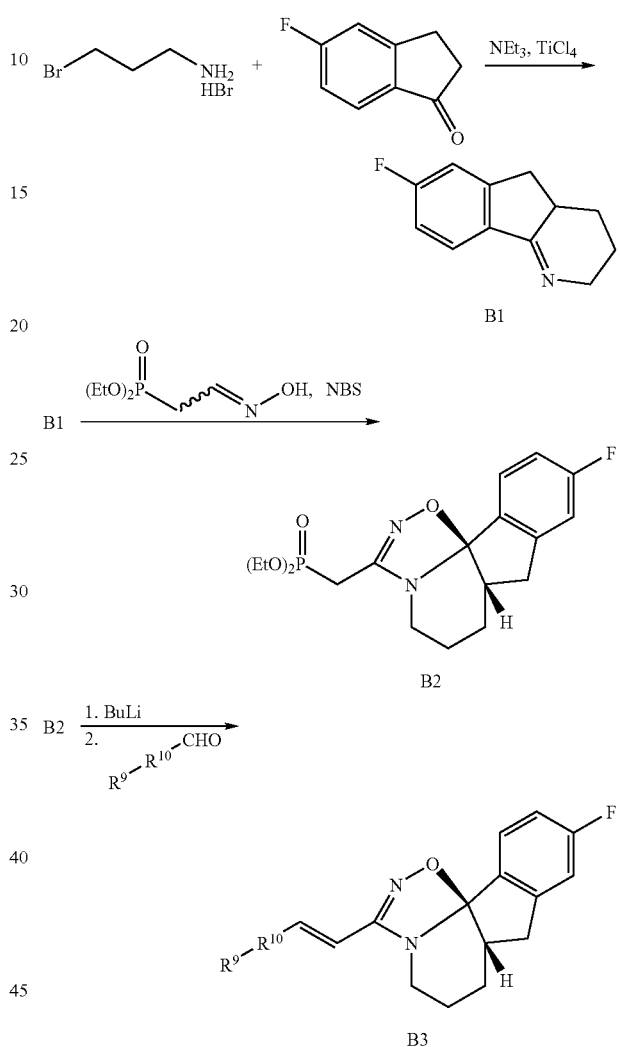

Method B, Step 1: 7-Fluoro-3,4,4a,5-tetrahydro-2H-indeno[1,2-b]pyridine (B1)

3-Bromopropylamine (4.7 g, 21.7 mmole) and 5-Fluoro-1-indanone (2.5 g, 16.7 mmole) were dissolved in 50 ml DMF and the reaction was cooled to 0° C. Triethylamine (13.5 g, 133 mmole) was added. 20 ml DCM was also added to help with the stirring. Titanium chloride (1M in DCM, 15 ml) was then added and the ice bath was removed. The reaction was stirred at room temperature overnight. 200 ml ether was added and the reaction was filtered though a Celite cake. The filtrate was concentrated to dryness under vacuum. The residue was dissolved in 200 ml ether and washed with brine (2×200 ml). The organic layer was dried over sodium sulfate and concentrated to dryness. 2.6 g Black oil was obtained and it was used in next step without further purification.

Method B, Step 2: Step 2: Diethyl ((7aS,12a1R)-10-fluoro-6,7,7a,8-tetrahydro-5H-indeno[1,2-b][1,2,4]oxadiazolo[4,5-a]pyridin-3-yl)methylphosphonate (B2)

Diethyl 2-(hydroxyimino)ethylphosphonate (1.87 g, 9.63 mmole) was dissolved in 30 ml DMF and the reaction was cooled to 0° C. N-bromosuccinimide (1.71 g, 9.63 mmole) in 15 ml DMF was added and the reaction was stirred at 0° C. for half hour. B1 (2.6 g, 9.63 mmole) and triethylamine (0.96 g, 9.6 mmole) in 25 ml DMF was added. The reaction was stirred at room temperature overnight. DMF was removed and the residue was partitioned between 100 ml EtOAc and 100 ml water. The organic layer was washed with water (2×100 ml), dried with $Na_2SO_4$ and concentrated. The residue was purified by column (EtOAc/hexane from 25/75 to 100/0 in 45 minutes, 120 g silica). Yield: 0.64 g, 17%. $^1$H NMR ($CDCl_3$ 400 MHz): 7.43 (dd, J=8.1, 5.1 Hz, 1H), 6.97 (m, 2H), 4.23 (m, 4H), 3.76 (m, 1H), 3.26 (dd, J=15.4 and 5.9 Hz, 1H), 2.80-3.10 (m, 3H), 2.55 (m, 1H), 2.34 (d, J=16.1 Hz, 1H), 2.30, (m, 1H), 1.50 (m, 2H), 1.38 (t, J=7.3 Hz, 6H), 1.05 (m, 1H).

Method B, Step 3: (7aS,12a1R)-10-fluoro-3-(3-methoxy-4-(4-methyl-1H-imidazol-1-yl)styryl)-6,7,7a,8-tetrahydro-5H-indeno[1,2-b][1,2,4]oxadiazolo[4,5-a]pyridine (B3, $R^9$=4-(4-Methylimidazol-1-yl), $R^{10}$=3-MeO-Phenyl)

B2 (0.24 g, 0.63 mmole) was dissolved in THF and the reaction was cooled to −78° C. n-Butyllithium (2.5 ml in Hexane, 0.28 ml) was added and the reaction was stirred at −78° C. for 30 minutes. 3-methoxy-4-(4-methyl-1H-imidazol-1-yl)benzaldehyde (0.136 g, 0.63 mmole) in 10 ml THF (Pre-cooled to −78° C.) was added. The reaction was stirred at −78° C. for 1 hour, then at room temperature for one hour. THF was removed and the residue was partitioned between 100 ml EtOAc and 100 ml water. The organic layer was washed with water (2×100 ml), dried with $Na_2SO_4$ and concentrated. The residue was purified by column (EtOAc/hexane from 25/75 to 100/0 in 45 minutes, 120 g silica). Yield: 0.19 g, 68%. $^1$H NMR ($CDCl_3$ 400 MHz): 7.73 (s, 1H), 7.50 (dd, J=8.1, 5.12 Hz, 1H), 7.43 (d, J=16.8 Hz, 1H), 7.27 (m, 1H), 7.18 (d, J=8.1 Hz, 1H), 7.13 (s, 1H), 7.00 (m, 3H), 6.52 (d, J=16.1 Hz, 1H), 3.90 (s, 3H), 3.71 (m, 1H), 3.30 (dd, J=16.1 and 5.9 Hz, 1H), 2.91 (m, 1H), 2.64 (m, 1H), 2.38 (d, J=16.1 Hz, 1H), 2.30 (s, 3H), 2.06, (m, 1H), 1.51 (m, 2H), 1.10 (m, 1H). MS (M+1): 445.2.

Compounds 19-21 in Table 1 were synthesized using methods similar to that of method B. Starting from 2-(tert-butyldimethylsilyloxy)-1-(4-fluorophenyl)ethanone, compounds 16 and 17 in Table 1 were synthesized using methods similar to that of method B.

Method C

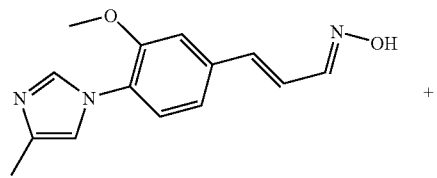

C1

+

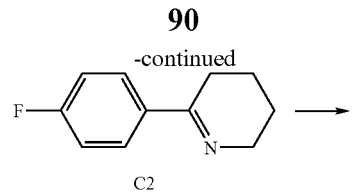

C2

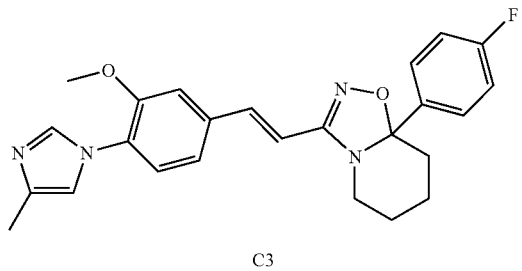

C3

To a dichloromethane solution of C1 is added 1 eq of N-chlorosuccinimide, and the solution is stirred until the disappearance of C1 monitored by a reverse phase HPLC system. To this solution is added C2 (1 eq) and the solution is stirred overnight to generate compound C3, which is isolated by methods known to those with ordinary skill in the art.

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-W02 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody W02 coated PS20 ProteinChip array. Mass spectra of Aβ captured on the array were read on SELDI ProteinChip Reader (Bio-Rad) according to manufacture's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Meso Scale Discovery) and biotin-4G8. The ECL signal was measured using Sector Imager 2400 (Meso Scale Discovery).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra are acquired in the linear mode with an acceleration voltage of 20 kV. Each spectrum presented in this work represents an average of 256 laser shots. To prepare the sample-matrix solution, 1 μL of immunoprecipitated A☐ sample is mixed with 3 μL of saturated α-cyano-4-hydroxycinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

Compounds 1, 2, and 9 to 12 had a Cellular Ab42 IC50 in the range of 200 nM to 20,000 nM, with an Ab total to Ab42 selectivity in the range of 100 to 6 fold.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula

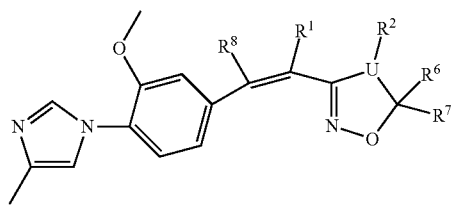

or a pharmaceutically acceptable salt thereof, wherein

U is N or —CH;

$R^1$ is hydrogen, alkyl, alkenyl, or alkoxy;

$R^2$ and $R^6$ are joined together to form 1) a 5-7 membered cycloalkyl ring, optionally substituted with —OH, or 2) a heterocyclyl ring optionally fused with an aryl ring;

$R^7$ is a 1) hydrogen, 2) an alkyl, or 3) a phenyl ring optionally substituted with 1-3 halo; and $R^8$ is hydrogen, alkyl, alkenyl, or alkoxy.

2. The compound according to claim 1 or a pharmaceutically acceptable salt thereof, wherein U is N.

3. The compound according to claim 1 or a pharmaceutically acceptable salt thereof, wherein U is —CH.

4. The compound according to claim 1 or a pharmaceutically acceptable salt thereof, wherein the halo is fluoro.

5. The compound according to claim 1 or a pharmaceutically acceptable salt thereof, wherein $R^1$ and $R^8$ are hydrogen.

6. The compound according to claim 1 or a pharmaceutically acceptable salt thereof, wherein the cycloalkyl ring formed by $R^2$ and $R^6$ is a cyclopentyl ring or cyclohexyl ring.

7. The compound according to claim 1 or a pharmaceutically acceptable salt thereof, wherein $R^2$ and $R^6$ join together to form a heterocyclyl ring.

8. The compound according to claim 7 or a pharmaceutically acceptable salt thereof, wherein the heterocyclyl ring is selected from pyrrolidinyl, piperidinyl, pyridazinyl, piperazinyl, morpholinyl, isoxazolidinyl, tetrahydrofuranyl and tetrahydropyranyl.

9. The compound according to claim 1 or a pharmaceutically acceptable salt thereof, wherein the compound is selected from the group consisting of:

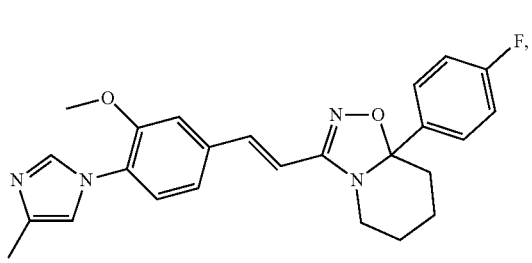

1

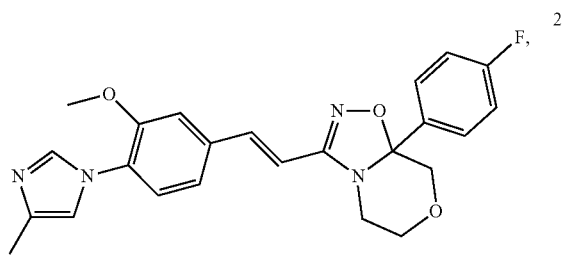

2

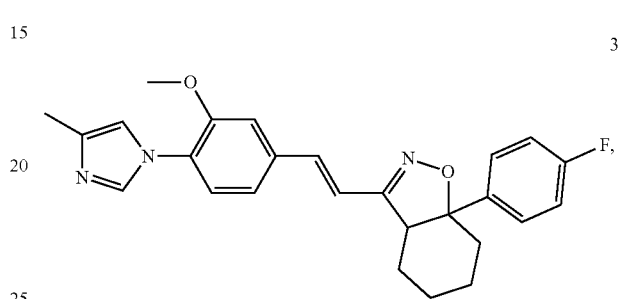

3

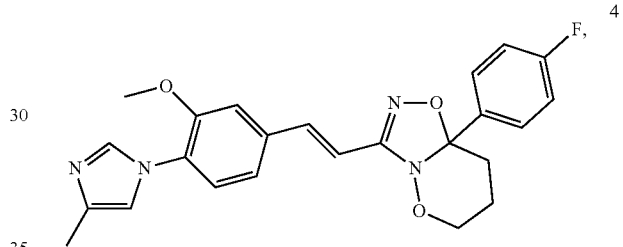

4

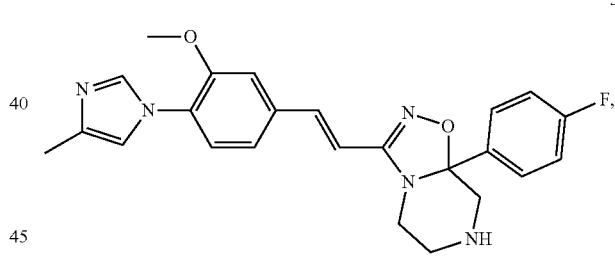

5

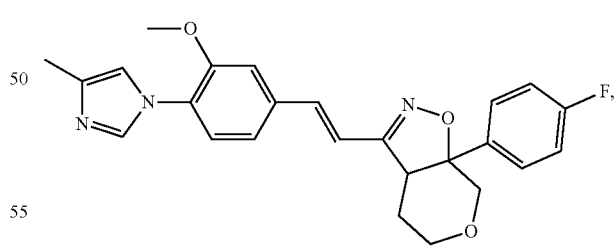

6

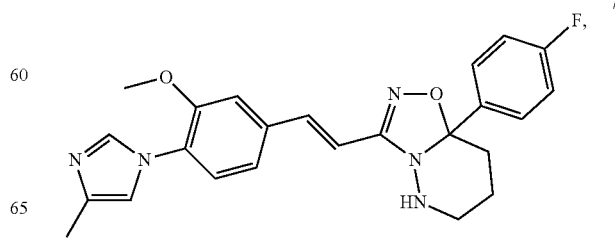

7

-continued

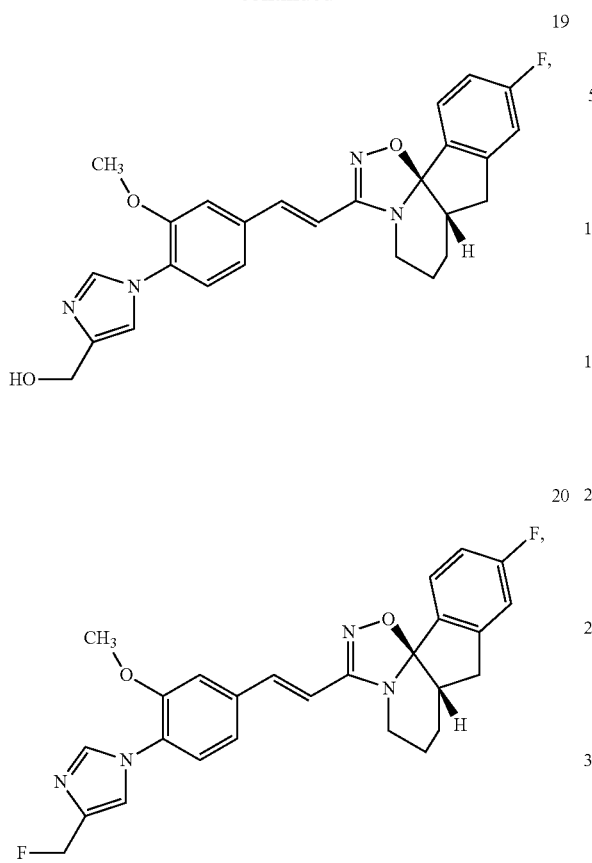
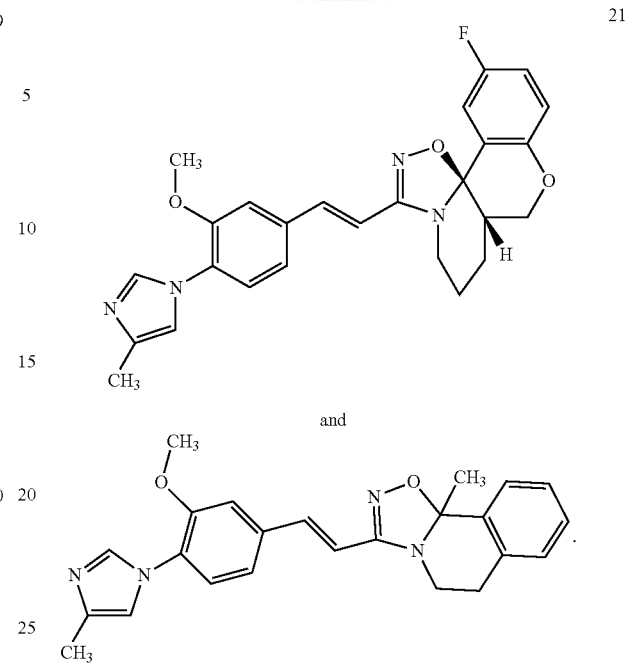
10. A pharmaceutical composition comprising a compound according to claim 1 or a pharmaceutically acceptable salt thereof, and a pharmaceutically acceptable carrier.
11. A pharmaceutical composition comprising a compound according to claim 5 or a pharmaceutically acceptable salt thereof, and a pharmaceutically acceptable carrier.
* * * * *